United States Patent
Ozes et al.

(10) Patent No.: US 7,407,973 B2
(45) Date of Patent: Aug. 5, 2008

(54) USE OF PIRFENIDONE IN THERAPEUTIC REGIMENS

(75) Inventors: Osman N. Ozes, San Bruno, CA (US); Lawrence M. Blatt, San Francisco, CA (US); Scott D. Seiwert, Pacifica, CA (US)

(73) Assignee: Intermune, Inc., Brisbane, CA (US)

( * ) Notice: Subject to any disclaimer, the term of this patent is extended or adjusted under 35 U.S.C. 154(b) by 0 days.

(21) Appl. No.: 10/574,631

(22) PCT Filed: Oct. 21, 2004

(86) PCT No.: PCT/US2004/035390

§ 371 (c)(1), (2), (4) Date: Jan. 31, 2007

(87) PCT Pub. No.: WO2005/040758

PCT Pub. Date: May 6, 2005

(65) Prior Publication Data

US 2007/0117841 A1    May 24, 2007

Related U.S. Application Data

(60) Provisional application No. 60/514,052, filed on Oct. 24, 2003.

(51) Int. Cl.
*A61K 31/445* (2006.01)

(52) U.S. Cl. .................................... 514/327

(58) Field of Classification Search ........................ None
See application file for complete search history.

(56) References Cited

U.S. PATENT DOCUMENTS 3,547,119 A    12/1970    Hall (Continued)

FOREIGN PATENT DOCUMENTS

EP    590267    5/2002

(Continued)

OTHER PUBLICATIONS

Hawk et al., Primary Cancer Prevention Trials, Hematology/Oncology Clinics of North America, vol. 14, No. 4, Aug. 2000, pp. 809-830.*

(Continued)

*Primary Examiner*—Raymond J Henley, III
(74) *Attorney, Agent, or Firm*—Marshall, Gerstein & Borun LLP; Carolyn Tang

(57) ABSTRACT

The present invention provides methods for treating a disorder, and methods for inhibiting a stress-activated protein kinase (SAPK) in a cell in an individual, the methods generally involving administering to an individual in need thereof an effective amount of pirfenidone or a pirfenidone analog; comparing a post-treatment SAPK activity level in a biological sample from the individual with a pre-treatment SAPK activity level; and adjusting the dose of the pirfenidone or pirfenidone analog based on the results of the comparison step. The present invention provides methods for treating a disorder, and methods for inhibiting a SAPK in a cell in an individual, the methods generally involving administering to an individual in need thereof an effective amount of pirfenidone or a pirfenidone analog; comparing a second post-treatment SAPK activity level in a biological sample from the individual with a first post-treatment SAPK activity level; and adjusting the dose of the pirfenidone or pirfenidone analog based on the results of the comparison step.

18 Claims, 6 Drawing Sheets

U.S. PATENT DOCUMENTS

| | | |
|---|---|---|
| 3,760,984 A | 9/1973 | Theeuwes |
| 3,839,346 A | 10/1974 | Gadekar |
| 3,845,770 A | 11/1974 | Theeuwes et al. |
| 3,916,899 A | 11/1975 | Theeuwes et al. |
| 3,923,426 A | 12/1975 | Theeuwes |
| 3,974,281 A | 8/1976 | Gadekar |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,042,699 A | 8/1977 | Gadekar |
| 4,052,509 A | 10/1977 | Gadekar |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,311,137 A | 1/1982 | Gerard |
| 4,327,725 A | 5/1982 | Cortese et al. |
| 4,350,155 A | 9/1982 | Thompson |
| 4,360,019 A | 11/1982 | Portner et al. |
| 4,487,603 A | 12/1984 | Harris |
| 4,531,937 A | 7/1985 | Yates |
| 4,627,850 A | 12/1986 | Deters et al. |
| 4,692,147 A | 9/1987 | Duggan |
| 4,695,623 A | 9/1987 | Stabinsky |
| 4,725,852 A | 2/1988 | Gamblin et al. |
| 4,741,900 A | 5/1988 | Alvarez et al. |
| 4,755,173 A | 7/1988 | Konopka et al. |
| 4,810,804 A | 3/1989 | Chandraratna |
| 4,865,845 A | 9/1989 | Eckenhoff et al. |
| 4,897,471 A | 1/1990 | Stabinsky |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |
| 5,200,534 A | 4/1993 | Rao |
| 5,229,529 A | 7/1993 | Ueno et al. |
| 5,234,692 A | 8/1993 | Magruder et al. |
| 5,234,693 A | 8/1993 | Magruder et al. |
| 5,274,137 A | 12/1993 | Nicolaou et al. |
| 5,279,949 A | 1/1994 | Nair |
| 5,283,253 A | 2/1994 | Holton et al. |
| 5,294,637 A | 3/1994 | Chen et al. |
| 5,310,562 A | 5/1994 | Margolin |
| 5,382,657 A | 1/1995 | Karasiewicz et al. |
| 5,395,760 A | 3/1995 | Smith et al. |
| 5,399,586 A | 3/1995 | Davies et al. |
| 5,415,869 A | 5/1995 | Straubinger et al. |
| 5,443,450 A | 8/1995 | Kratoska et al. |
| 5,466,861 A | 11/1995 | Dawson et al. |
| 5,518,729 A | 5/1996 | Margolin |
| 5,605,690 A | 2/1997 | Jacobs et al. |
| 5,643,207 A | 7/1997 | Rise |
| 5,643,575 A | 7/1997 | Martinez et al. |
| 5,672,662 A | 9/1997 | Harris et al. |
| 5,690,925 A | 11/1997 | Gray et al. |
| 5,716,632 A | 2/1998 | Margolin |
| 5,728,396 A | 3/1998 | Peery et al. |
| 5,770,378 A | 6/1998 | Hwang et al. |
| 5,770,382 A | 6/1998 | Hwang et al. |
| 5,770,383 A | 6/1998 | Hwang et al. |
| 5,780,676 A | 7/1998 | Boehm et al. |
| 5,814,019 A | 9/1998 | Steinbach et al. |
| 5,820,589 A | 10/1998 | Torgerson et al. |
| 5,821,263 A | 10/1998 | Scola et al. |
| 5,824,685 A | 10/1998 | Campochiaro et al. |
| 5,824,701 A | 10/1998 | Greenwald et al. |
| 5,869,680 A | 2/1999 | Mas et al. |
| 5,951,974 A | 9/1999 | Gilbert et al. |
| 5,962,478 A | 10/1999 | Margolin |
| 5,976,109 A | 11/1999 | Heruth |
| 5,981,709 A | 11/1999 | Greenwald et al. |
| 5,985,265 A | 11/1999 | Kinstler et al. |
| 5,985,305 A | 11/1999 | Peery et al. |
| 6,017,328 A | 1/2000 | Fischell et al. |
| 6,046,305 A | 4/2000 | Choi |
| 6,090,822 A | 7/2000 | Margolin |
| 6,171,276 B1 | 1/2001 | Lippe et al. |
| 6,198,966 B1 | 3/2001 | Heruth |
| 6,214,542 B1 | 4/2001 | Striker et al. |
| 6,214,854 B1 | 4/2001 | Wang et al. |
| 6,241,704 B1 | 6/2001 | Peterson et al. |
| 6,300,349 B1 | 10/2001 | Margolin |
| 6,464,687 B1 | 10/2002 | Ishikawa et al. |
| 6,475,180 B2 | 11/2002 | Peterson et al. |
| 6,489,325 B1 | 12/2002 | Adams et al. |
| 6,492,395 B1 | 12/2002 | Scheiwe et al. |
| 6,497,871 B1 | 12/2002 | Gray et al. |
| 6,512,954 B2 | 1/2003 | Fox et al. |
| 6,541,447 B1 | 4/2003 | Dawson |
| 6,548,520 B1 | 4/2003 | Adams et al. |
| 6,569,871 B1 | 5/2003 | Adams et al. |
| 6,579,856 B2 | 6/2003 | Mercola |
| 6,680,335 B2 | 1/2004 | Tang |
| 6,943,161 B2 | 9/2005 | Erickson et al. |
| 2001/0036955 A1 | 11/2001 | Gerritsen et al. |
| 2002/0156023 A1 | 10/2002 | Walling et al. |

FOREIGN PATENT DOCUMENTS

| | | |
|---|---|---|
| WO | WO 90/04036 | 4/1990 |
| WO | WO 90/10077 | 9/1990 |
| WO | WO 92/02190 | 2/1992 |
| WO | WO 93/10076 | 5/1993 |
| WO | WO 93/23555 | 11/1993 |
| WO | WO 94/07876 | 4/1994 |
| WO | WO 94/07880 | 4/1994 |
| WO | WO 94/07881 | 4/1994 |
| WO | WO 94/07882 | 4/1994 |
| WO | WO 97/03106 | 1/1997 |
| WO | WO 97/25428 | 7/1997 |
| WO | WO 97/27840 | 8/1997 |
| WO | WO 98/13059 | 4/1998 |
| WO | WO 98/22451 | 5/1998 |
| WO | WO 98/58927 | 12/1998 |
| WO | WO 99/09021 | 2/1999 |
| WO | WO 99/14209 | 3/1999 |
| WO | WO 99/18113 | 4/1999 |
| WO | WO 01/36001 | 5/2001 |

OTHER PUBLICATIONS

Cecil, Textbook of Medicine, 21st ed., vol. 1, published 2000 by W.B Saunders Company (PA), pp. 1060-1074.*
Medline Abstract No. 97217050, Kumar, Indian Journal of Experimental Biology, (May 1996) 34(5), 391-402.*
Medline Abstract No. 96432582, Oka et al., Japanese Journal of Pharmacology, (Jun. 1996) 71(2), 89-100.*
Medline Abstract No. 97074593, Smith et al., CA: A Cancer Journal for Clinicians, (Nov.-Dec. 1996), 46(6), 343-363.*
Medline Abstract No. 1998029329, Rickels et al., Journal of Clinical Psychiatry, (1997) 58 Suppl. 11, 4-10.*
Auerbach et al., "Assays for Angiogenesis: A Review", Pharmac. Ther., 51:1-11, 1991.
Baert et al., "Tumor Necrosis Factor α Antibody (Infliximab) Therapy Profoundly Down-regulates the Inflammation in Crohn's Ileocolitis", Gastroenterology, 116:22-28, 1999.
Brunt, "Grading and Staging the Histopathological Lesions of Chronic Hepatitis: The Knodell Histology Activity Index and Beyond", Hepatology, 31:241-246, 2000.
Chamow et al., "Modification of CD4 Immunoadhesin with Monomethoxypoly(ethylene glycol) Aldehyde via Reductive Alkylation", Bioconj. Chem., 5:133-140, 1994.

Elliott et al., "Treatment of Rheumatoid Arthritis with Chimeric Monoclonal Antibodies to Tumor Necrosis Factor α", Arthritis Rheum., 36:1681-1690, 1993.

Elliott et al., "Randomised double-blind comparison of chimeric monoclonal antibody to tumor necrosis factor α(cA2) versus placebo in rheumatoid arthritis", Lancet, 344:1105-1110, 1994.

Forrer et al., "Enzyme-linked immunosorbent assay for measurement of JNK, ERK, and p38 Kinase Activities", Biol. Chem., 379:1101-1111, 1998.

Friedler et al., "Development of a functional backbone cyclic mimetic of the HIV-1 Tat Arginine-rich Motif", J. Biol. Chem., 275:23783-23789, 2000.

Gray et al., "Expression of human immune interferon cDNA in E. coli and monkey cells", Nature, 295:503-508, 1982.

Ishak, "Histological grading and staging of chronic hepatitis", J. Hepatol, 22:696-699, 1995.

Knodell, "Formulation and application of a numerical scoring system for assessing histological activity in asymptomatic chronic active hepatitis", Hepatology, 1:431-435, 1981.

Lee et al., "A protein kinase involved in the regulation of inflammatory cytokine biosynthesis", Nature, 372:739-746, 1994.

Li et al., "Angiostatis steroids potentiated by sulfated cyclodextrins inhibit corneal neovascularization", Invest. Opthalmol. Vis. Sci., 32:2898-2905, 1991.

Masci et al., "New and modified interferon alfas: preclinical and clinical data", Curr. Oncol. Rep., 5:108-113, 2003.

Masseroli et al., "Design and validation of a new image analysis method for automatic quantification of interstitial fibrosis and glomerular morphometry", Lab. Invest., 78:511-522, 1998.

Metavir, "Intraobserver and interobserver variations in liver biopsy interpretation in patients with chronic hepatitis C", Hepatology, 20:15-20, 1994.

Miller et al., "Vascular endothelial growth factor/vascular permeability factor is temporarily and spatially correlated with ocular angiogenesis in a primate model", Am. J. Pathol., 145:574-584, 1994.

Mohler et al., "Soluble tumor necrosis factor (TNF) receptors are effective therapeutic agents in lethal endotoxemia and function simultaneously as both TNF carriers and TNF antagonists", J. Immunol., 151:1548-1561, 1993.

Nicolaou et al., "Calicheamicin $0^1_1$: A rationally designed molecule with extremely potent and selective DNA cleaving properties and apoptosis including activity", Angew Chem. Int. Ed. Engl., 33:183-186, 1994.

O'Reilly et al., "Angiostatin: A novel angiogenesis inhibitor that mediates the suppression of metastases by a Lewis lung carcinoma", Cell, 79:315-328, 1994.

Osborn et al., "Pharmacokinetic and pharmacodynamic studies of a human serum albumin-interferon-α fusion protein in cynomolgus monkeys", J. Pharmacol. Exp. Therap., 303:540-548, 2002.

Park et al., "Pharmacology of Escherichia coli-L-asparaginase polyethylene glycol adduct", Anticancer Res., 1:373-376, 1981.

Piascik, "New antibody approved for treatment of rheumatoid arthritis", J. Am. Pharm. Assoc., 43:327-328, 2003.

Rinderknecht et al., "Natural Human Interferon-γ", J. Biol. Chem., 259:6790-6797, 1984.

Ryu et al., "Idiopathic pulmonary fibrosis: current concepts", Mayo Clin. Proc., 73:1085-1101, 1998.

Scheuer, "Classification of chronic viral hepatitis: a need for reassessment", J. Hepatol., 13:372-374, 1991.

Sheppard et al., "IL-28, IL-29 and their class II cytokine receptor IL-28R", Nature, 4:63-68, 2003.

Smith et al., "A receptor for tumor necrosis factor defines an unusual family of cellular and viral proteins", Science, 248:1019-1023, 1990.

Sun et al., "Design, synthesis, and evaluations of substituted 3-[(3- or 4-carboxyethylpyrrol-2-yl)methylidenyl]indolin-2-ones as inhibitors of VEGF, FGF, and PDGF receptor tyrosine kinases", J. Med. Chem., 42:5120-5130, 1999.

Sun et al., "Identification of substituted 3-[(4,5,6,7-tetrahydro-1H-indol-2-yl)methylene]-1,3-dihydroindol-2-ones as growth factor receptor inhibitors for VEGF-R2 (Flk-1/KDR), FGF-R1, and PDGF-Rβ tyrosine kinases", J. Med. Chem., 43:2655-2663, 2000.

International Search Report for PCT/US2004/035390 mailed Jun. 1, 2005.

Written Opinion of the International Searching Authority (US), mailed Jun. 1, 2005 for PCT/US2004/035390.

* cited by examiner

USE OF PIRFENIDONE IN THERAPEUTIC REGIMENS

FIELD OF THE INVENTION

The present invention is in the field of treating various disorders comprising administering pirfenidone or a pirfenidone analog, and in particular comprising administering pirfenidone or a pirfenidone analog to an individual; detecting a stress-activated protein kinase level in a biological sample from the individual; and adjusting the dose of pirfenidone or pirfenidone analog accordingly.

BACKGROUND OF THE INVENTION

The signal transduction pathways that use mitogen-activated protein (MAP) kinases have an important role in a variety of cellular responses, including growth, stress-induced gene expression, and compensation for alterations in the environment. The Stress-Activated Protein Kinase or SAPK group of MAPKs includes the c-Jun N-terminal Kinase (JNK) and p38. SAPKs are activated strongly in response to environmental stresses such as heat and osmotic shock, UV-irradiation, exposure to genotoxic agents and pro-inflammatory cytokines. In mammalian cells, the JNK and p38 signalling pathways are involved in the response of cells to stresses such as those induced by ischaemia and reperfusion injury, they play a role in the immune response and also in the regulation of apoptosis. The p38 group of MAPK include at least four members, designated p38 or p38α, p38β, p38γ, and p38δ. Several downstream substrates of p38 have been identified, including transcription factors, protein kinases, and enzymes. Studies have indicated that activation of the p38 pathway is involved in many pathologic changes that occur during inflammatory, immunologic, and cardiovascular diseases.

There is a need in the art for improved treatment methods for various disorders such that dosage levels are adjusted based on a patient's response. The present invention addresses this need.

Literature

U.S. Pat. No. 6,579,856; U.S. Pat. No. 5,962,478; U.S. Pat. No. 6,300,349.

SUMMARY OF THE INVENTION

The present invention provides methods for treating a disorder, and methods for inhibiting a stress-activated protein kinase (SAPK) in a cell in an individual, the methods generally involving administering to an individual in need thereof an effective amount of pirfenidone or a pirfenidone analog; comparing a post-treatment SAPK activity level in a biological sample from the individual with a pre-treatment SAPK activity level; and adjusting the dose of the pirfenidone or pirfenidone analog based on the results of the comparison step. The present invention provides methods for treating a disorder, and methods for inhibiting a SAPK in a cell in an individual, the methods generally involving administering to an individual in need thereof an effective amount of pirfenidone or a pirfenidone analog; comparing a second post-treatment SAPK activity level in a biological sample from the individual with a first post-treatment SAPK activity level; and adjusting the dose of the pirfenidone or pirfenidone analog based on the results of the comparison step.

DEFINITIONS

Figure 1:
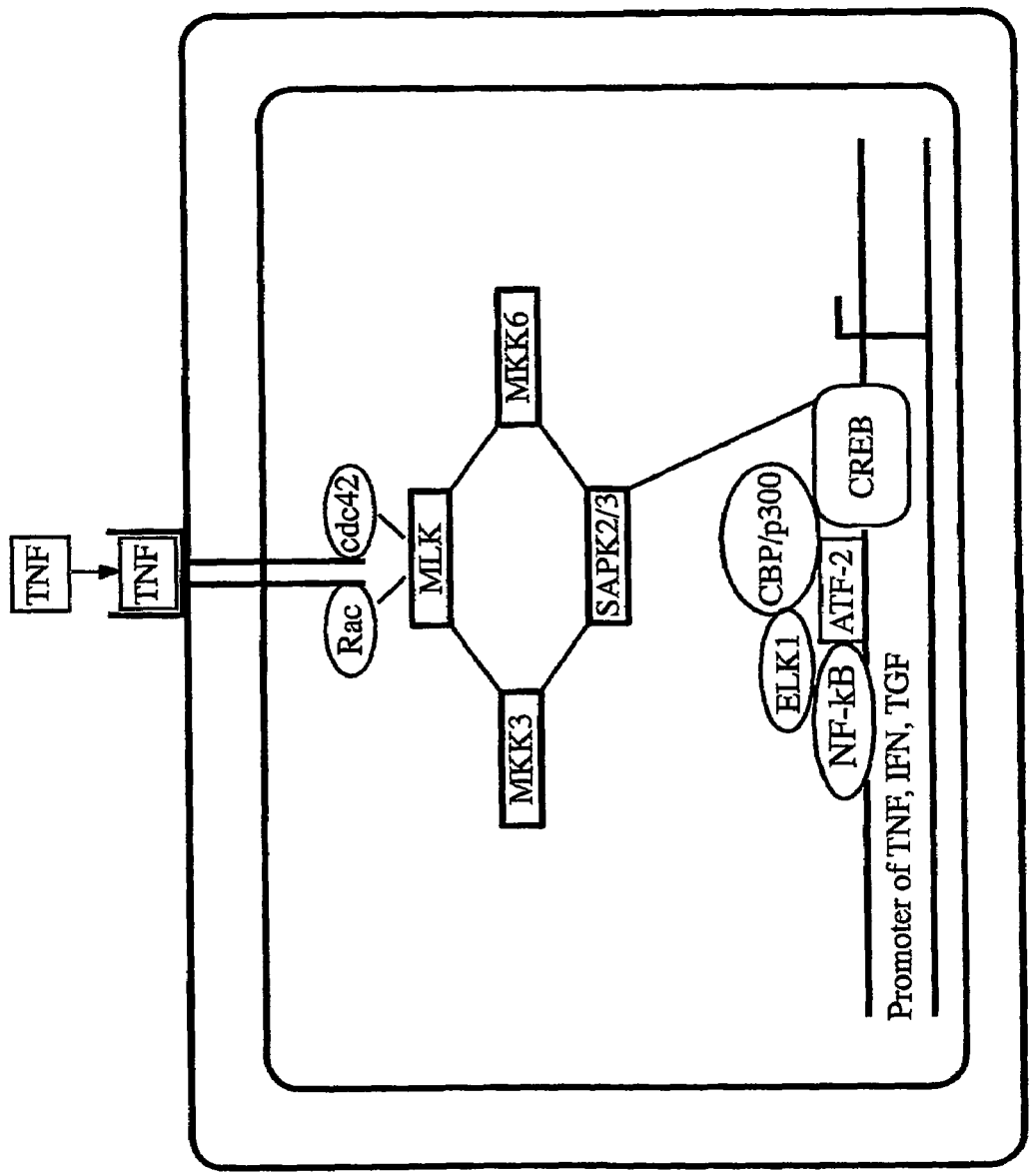
FIG. 1 depicts various downstream signaling events that are triggered by TNF binding to a TNF receptor.
Figure 2:
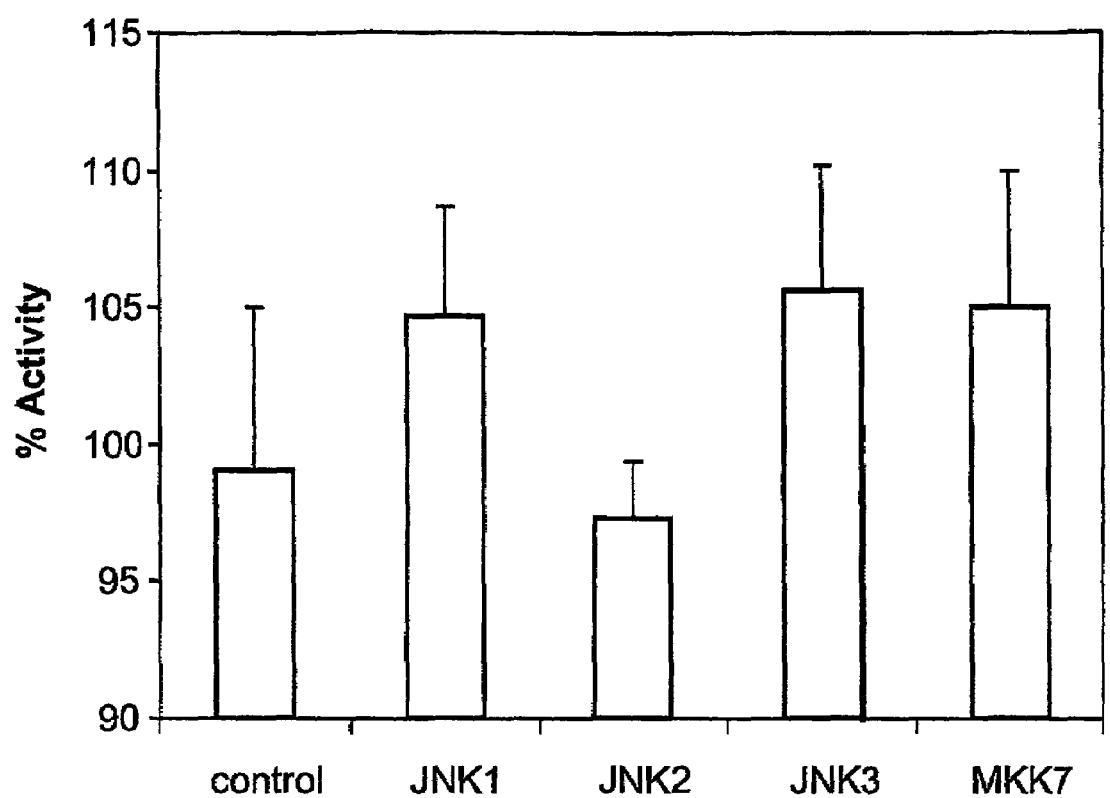
FIG. 2 depicts the effect of pirfenidone on the enzymatic activity of c Jun kinases (JNK).
Figure 3:
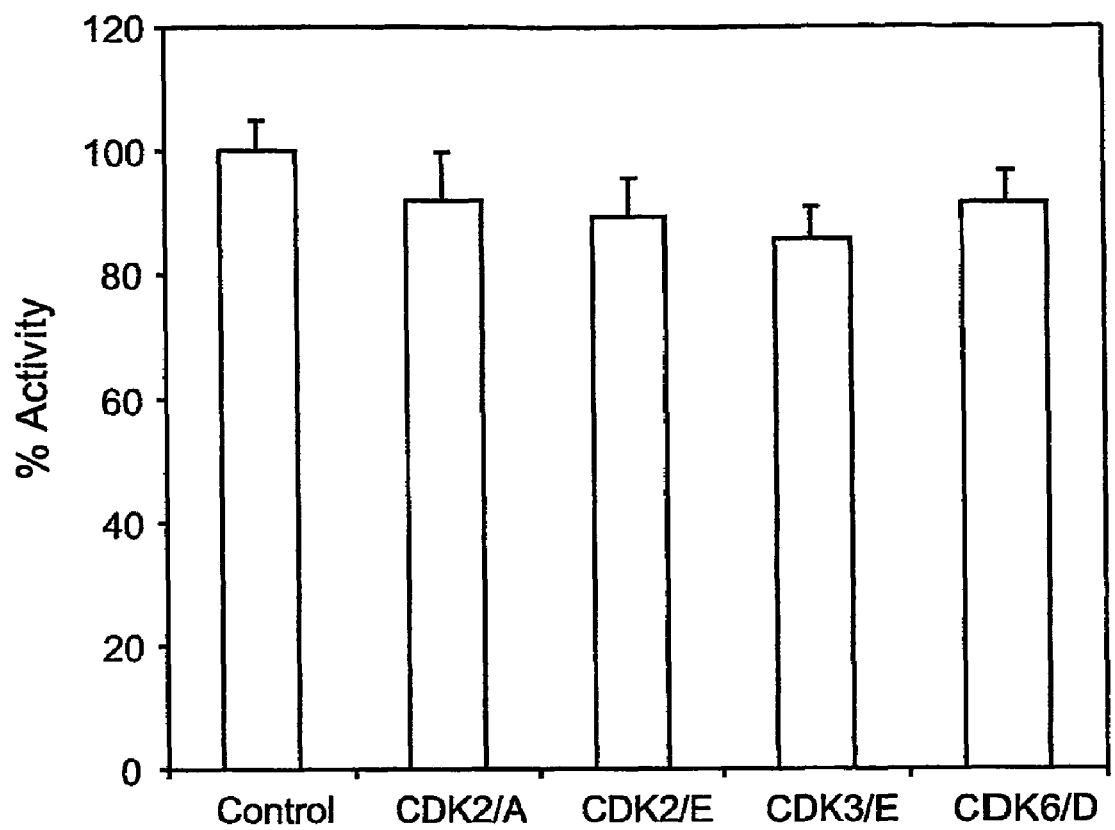
FIG. 3 depicts the effect of pirfenidone on the enzymatic activity of various cyclin dependent kinases (CDK).
Figure 4:
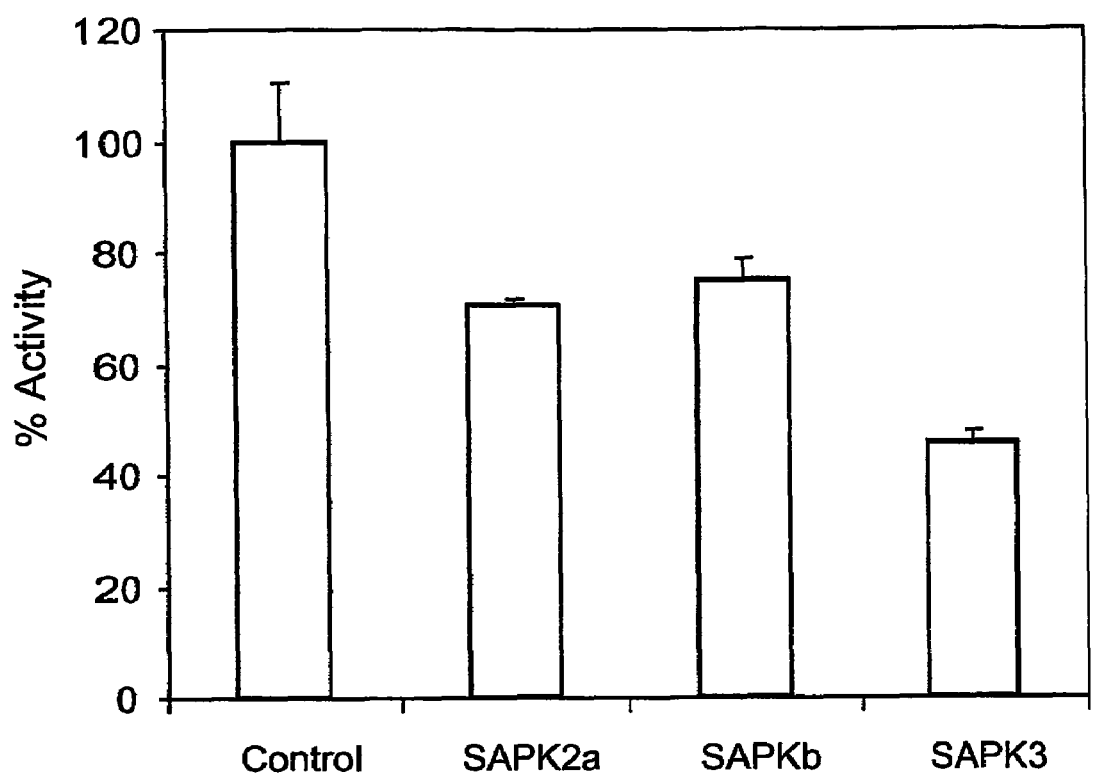
FIG. 4 depicts the effect of pirfenidone on the enzymatic activity of various stress-activated protein kinases.
Figure 5:
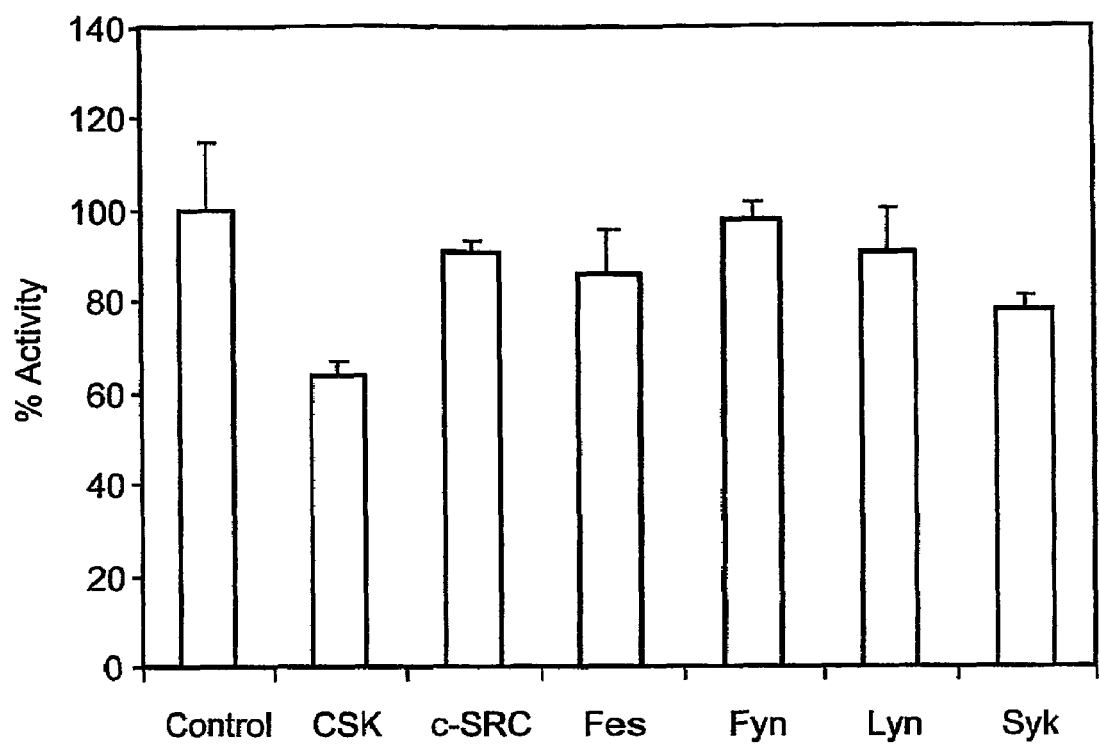
FIG. 5 depicts the effect of pirfenidone on the enzymatic activity of various SRC protein kinases.

The terms "individual," "host," "subject," and "patient" are used interchangeably herein, and refer to a mammal, including, but not limited to, primates, including simians and humans.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, any compound or agent described as "effective for the avoidance or amelioration of side effects induced by pirfenidone or a pirfenidone analog," or as "effective for reducing or eliminating the severity or occurrence of side effects induced by pirfenidone or a pirfenidone analog," or any compound or agent described by language with a meaning similar or equivalent to that of either of the foregoing quoted passages, is/are defined as a compound(s) or agent(s) that when co-administered to a patient in an effective amount along with a given dosing regimen of a pirfenidone or a pirfenidone analog, abates or eliminates the severity or occurrence of side effects experienced by a patient in response to the given dosing regimen of the pirfenidone/pirfenidone analog therapy, as compared to the severity or occurrence of side effects that would have been experienced by the patient in response to the same dosing regimen of the combination therapy without co-administration of the agent.

As used herein, any compound or agent described as "effective for the avoidance or amelioration of side effects induced by a Type II interferon receptor agonist," or as "effective for reducing or eliminating the severity or occurrence of side effects induced by a Type II interferon receptor agonist," or any compound or agent described by language with a meaning similar or equivalent to that of either of the foregoing quoted passages, is/are defined as a compound(s) or agent(s) that when co-administered to a patient in an effective amount along with a given dosing regimen of a Type II interferon receptor agonist combination therapy, abates or eliminates the severity or occurrence of side effects experienced by a patient in response to the given dosing regimen of the Type II interferon receptor agonist, as compared to the severity or occurrence of side effects that would have been experienced by the patient in response to the same dosing regimen of the combination therapy without co-administration of the agent.

As used herein, the term "a Type II interferon receptor agonist" refers to any naturally-occurring or non-naturally-occurring ligand of a human Type II interferon receptor which binds to and causes signal transduction via the receptor. Type II interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

A "fibrotic condition," "fibroproliferative condition," "fibrotic disease," "fibroproliferative disease," "fibrotic disorder," and "fibroproliferative disorder" are used interchangeably to refer to a condition, disease or disorder that is characterized by dysregulated proliferation or activity of fibroblasts and/or pathologic or excessive accumulation of collagenous tissue. Typically, any such disease, disorder or condition is amenable to treatment by administration of a compound having anti-fibrotic activity. Fibrotic disorders include, but are not limited to, pulmonary fibrosis, including idiopathic pulmonary fibrosis (IPF) and pulmonary fibrosis from a known etiology, liver fibrosis, and renal fibrosis. Other exemplary fibrotic conditions include musculoskeletal fibrosis, cardiac fibrosis, post-surgical adhesions, scleroderma, glaucoma, and skin lesions such as keloids.

The term "angiogenesis-mediated disease," "angiogenesis-mediated disorder," "angiogenic disease," and "angiogenic disorder" are used interchangeably to refer to any disease characterized by pathological neovascularization, including all solid tumors, rheumatoid arthritis, psoriasis, atherosclerosis, diabetic and other retinopathies, retrolental fibroplasia, age-related macular degeneration, neovascular glaucoma, hemangiomas, thyroid hyperplasias (including Grave's disease), an inflammatory bowel disease such as, for example, Crohn's disease or ulcerative colitis, and corneal transplantation.

The term "proliferative disorder" and "proliferative disease" are used interchangeably to refer to any disease or condition characterized by pathological cell growth or proliferation, including all fibroproliferative or fibrotic conditions, angiogenesis-mediated diseases, neoplastic disorders, and chronic inflammatory disorders mediated by dysregulated or unrestrained cellular proliferation.

The terms "cancer, "neoplasm, and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

The term "TNF-mediated disorder" includes, but is not limited to, nervous system syndromes, such as relapsing-remitting, multiple sclerosis, primary and secondary multiple sclerosis, spinal multiple sclerosis, cerebral malaria, viral or bacterial infections of the central nervous system, bacterial meningitis, "autoimmune" disorders of the central nervous system, central nervous system stroke and infarction, brain edema, Parkinson's syndrome, amyotrophic lateral sclerosis, brain concussion or contusion, musculo-skeletal syndrome, such as rheumatoid arthritis, trauma-induced arthritis, arthritis caused by a microbial infection, or by a parasite, tendonitis, arthritis induced by medical products or drugs (including, small synthetic molecules as well as purified natural or synthesized peptides or proteins), pulmonary syndromes, such as acute adult respiratory distress syndrome, asthma, allergic rhinitis, allergic generalized reactions, allergic conjunctivitis, chronic obstructive pulmonary disease, and lung sarcoidosis, systemic immunologic, inflammatory, or toxic syndromes, such as endotoxemia shock syndrome, septic shock, graft-host disease following, bone-marrow transplantation, hemorrhagic shock, reperfusion injury of the brain or myocardium, thermal burns, radiation injury, general or dermal traumatic or contusion injuries, eosinophilic granuloma, diabetes mellitus (Type 2), and systemic lupus erythromatosus, and gastrointestinal syndromes, such as Crohn's disease, ulcerative colitis, and liver inflammatory disorders.

As used herein, the term "interferon receptor agonist" refers to any agent that binds to an interferon receptor, which binding results in signal transduction via the receptor. Interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; chemical agonists; and the like.

As used herein, the term "alphavirus," and its grammatical variants, refers to a group of viruses characterized by (i) an RNA genome (ii) viral replication in the cytoplasm of host cells and (iii) no DNA phase occurs in the viral replication cycle.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

As used herein, the term "Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody agonists specific for an interferon receptor; non-peptide chemical agonists; and the like.

As used herein, the term "Type III interferon receptor agonist" refers to any naturally occurring or non-naturally occurring ligand of humanIL-28 receptor α ("IL-28R"), the amino acid sequence of which is described by Sheppard, et al., infra, that binds to and causes signal transduction via the receptor.

The term "dosing event" as used herein refers to administration of a therapeutic agent to a patient in need thereof, which event may encompass one or more releases of agent from a drug dispensing device.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type II interferon receptor agonist, e.g., IFN-γ) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery means delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

As used herein, the term "pirfenidone" means 5-methyl-1-phenyl-2-(1H)-pyridone. As used herein, the term "pirfenidone analog" means any compound of Formula I, IIA or IIB below. As used herein, the term "specific pirfenidone analog" refers to, and is limited to, each and every pirfenidone analog shown in Table 1.

As used herein, any compound or agent described as "effective for the avoidance or amelioration of side effects induced by a Type II interferon receptor agonist and/or pirfenidone or pirfenidone analog," or as "effective for reducing or eliminating the severity or occurrence of side effects induced by a Type II interferon receptor agonist and/or pirfenidone or pirfenidone analog," or any compound or agent described by language with a meaning similar or equivalent to that of either of the foregoing quoted passages, is/are defined as a compound(s) or agent(s) that when co-administered to a patient in an effective amount along with a given dosing regimen of a Type II interferon receptor agonist/pirfenidone or pirfenidone analog combination therapy, abates or eliminates the severity or occurrence of side effects experienced by a patient in response to the given dosing regimen of the Type II interferon receptor agonist/pirfenidone or pirfenidone analog combination therapy, as compared to the severity or occurrence of side effects that would have been experienced by the patient in response to the same dosing regimen of the Type II interferon receptor agonist/pirfenidone or pirfenidone analog combination therapy without co-administration of the agent.

The term "biological sample" encompasses a variety of sample types obtained from an individual and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The term "antineoplastic" agent, drug or compound is meant to refer to any agent, including any chemotherapeutic agent, biological response modifier (including without limitation (i) proteinaceous, i.e. peptidic, molecules capable of elaborating or altering biological responses and (ii) non-proteinaceous, i.e. non-peptidic, molecules capable of elaborating or altering biological responses), cytotoxic agent, or cytostatic agent, that reduces proliferation of a neoplastic cell.

The term "chemotherapeutic agent" or "chemotherapeutic" (or "chemotherapy", in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubincin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g. paclitaxel (TAXOL®, Bristol Meyers Squibb Oncology, Princeton, N.J.) and docetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

The term "anti-inflammatory" agent, drug or compound is meant to include agents prevent or reduce inflammation and include, for example, and IL-1 antagonists, such as IL-1Ra.

The term "anti-fibrotic agent," as used herein, includes any agent that reduces or treats fibrosis, including, but not limited to, an anti-angiogenic agent; a vascular endothelial growth factor (VEGF) antagonist; a basic fibroblast growth factor (bFGF) antagonist; a bFGF receptor antagonist; a transforming growth factor-beta (TGF-β) antagonist; a TGF-β receptor antagonist; a steroidal anti-inflammatory agent; and a non-pirfenidone TNF antagonist.

The term "non-pirfenidone TNF-α antagonist," as used herein, refers to tumor necrosis factor (TNF) antagonists, such as anti-TNF antibodies (e.g. REMICADE™ anti-TNF monoclonal antibody) and soluble TNF receptor (e.g. ENBREL™ TNF receptor-Ig immunoadhesin), and HUMIRA®.

The terms "angiogenic agent," "angiogenic compound," and "angiogenic factor" are meant to include agents that promote neovascularization, such as VEGF, bFGF, and TGF-beta The terms "anti-angiogenic" or "angiostatic" agent, drug or compound, or "angiogenesis inhibitor," are meant to include agents that prevent or reduce neovascularization, such as VEGF antagonists, VEGF receptor antagonists, bFGF antagonists, bFGF receptor antagonists, TGF-beta antagonists, and TGF-beta receptor antagonists.

The term "biological response modifier" refers to any proteinaceous (i.e., peptidic) molecule or any non-proteinaceous (i.e., non-peptidic) molecule capable of elaborating or altering a biological response relevant to the treatment of cancer. Examples of biological response modifiers include antagonists of tumor-associated antigens, such as anti-tumor antigen antibodies, antagonists of cellular receptors capable of inducing cell proliferation, agonists of cellular receptors capable of inducing apoptosis, such as Apo-2 ligands, growth factor cytokines, such as hematopoietic cytokines, including erythropoietins, such as EPOGEN™ epoetin-alfa, granulocyte colony stimulating factors (G-CSFs), such as NEUPOGEN™ filgrastim, granulocyte-macrophage colony stimulating factors (GM-CSFs), and thrombopoietins, lymphocyte growth factor cytokines, such as interleukin-2, and antagonists of growth factor cytokines, including EGF inhibitors, EGF receptor inhibitors, such as ERBITUX™ cetuximab, IRESSA™ gefitinib and TARCEVA™ erolotinib, and antagonists of angiogenic factors, e.g. vascular endothelial cell growth factor (VEGF) antagonists, such as AVASTIN™ bevacizumab (anti-VEGF monoclonal antibody).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a stress-activated protein kinase (SAPK)" includes a plurality of such SAPK, reference to "a SAPK inhibitor" includes a plurality of SAPK inhibitors, and reference to "the therapeutic agent" includes reference to one or more therapeutic agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based in part on the observation that pirfenidone inhibits enzymatic activity of stress-activated protein kinases (SAPK). Thus, pirfenidone is useful to treat any disorder amenable to treatment by inhibiting a SAPK in a cell of an individual. The invention provides methods of treating disorders amenable to treatment by inhibiting a SAPK. The methods involve monitoring a SAPK enzymatic activity level in an individual during the course of treatment with pirfenidone or pirfenidone analog and, based on the levels of SAPK activity, adjusting the dosage level of pirfenidone or pirfenidone analog. Where the SAPK activity level decreases following treatment, the dosage of pirfenidone or pirfenidone analog is adjusted based on the degree of that decrease.

Dose Monitoring and Dose Titering

The present invention provides methods for treating a viral infection; an inflammatory disorder; a TNF-mediated disorder; a proliferative disorder, including angiogenesis-mediated disorders, cancer, and fibrotic disorders, the methods generally involving administering to an individual in need thereof an effective amount of pirfenidone or a pirfenidone analog; monitoring the level of a SAPK in a biological sample from the individual (e.g., a pre-treatment sample and a post-treatment sample; a post-treatment sample taken at a first time and a post-treatment sample taken at a second time during the course of treatment; etc.); and adjusting the dose of the pirfenidone or pirfenidone analog based on the results of the monitoring step such that effective amounts of the pirfenidone or pirfenidone analog are administered to ameliorate the clinical course of disease. The terms "monitoring the level of SAPK activity," "detecting the level of SAPK activity," and "measuring the level of SAPK activity" are used interchangeably herein.

A subject method generally involves administering a first dosage of pirfenidone or a pirfenidone analog for a first period of time; comparing a post-treatment SAPK activity level with a pre-treatment SAPK activity level and/or comparing a second post-treatment SAPK activity level with a first post-treatment SAPK activity level; and adjusting the dosage of pirfenidone or pirfenidone analog based on the results of the comparison step. In some embodiments, a subject method involves pirfenidone or pirfenidone analog monotherapy. In other embodiments, a subject method involves pirfenidone or pirfenidone analog combination therapy with at least a second therapeutic agent. Suitable additional therapeutic agents include, but are not limited to, a Type I interferon receptor agonist, a Type II interferon receptor agonist, a Type III interferon receptor agonist, ribavirin, an anti-cancer agent (e.g., an anti-neoplastic agent, an anti-proliferative agent, a cytotoxic agent), an anti-angiogenic agent, an anti-inflammatory agent, an anti-fibrotic agent, a hematopoietic agent, and a non-pirfenidone TNFα antagonist. Combinations of two or more additional therapeutic agents are in some embodiments administered in combination therapy with pirfenidone or pirfenidone analog.

In some embodiments, the present invention provides methods of inhibiting a SAPK in a cell in an individual, the method generally involving administering to an individual in need thereof an effective amount of pirfenidone or a pirfenidone analog; monitoring the level of a SAPK in a biological sample from the individual (e.g., a pre-treatment sample and a post-treatment sample; a post-treatment sample taken at a first time and a post-treatment sample taken at a second time during the course of treatment; etc.); and adjusting the dose of the pirfenidone or pirfenidone analog based on the results of the monitoring step. The methods are useful for treating disorders amenable to treatment by inhibiting a SAPK, including, a viral infection, an inflammatory disorder, a TNF-mediated disorder, a proliferative disorder, including angiogenesis-mediated disorders, cancer, and fibrotic disorders.

In some embodiments, the present invention provides methods of inhibiting a SAPK in a cell in an individual, the method generally involving administering to an individual in need thereof an effective amount of pirfenidone or a pirfenidone analog; comparing a post-treatment level of SAPK activity in a biological sample from the individual to a pre-treatment level of SAPK activity; and adjusting the dose of the pirfenidone or pirfenidone analog based on the results of the comparison step. The comparison step involves detecting a pre-treatment SAPK activity level; detecting a post-treatment SAPK activity level; and comparing the post-treatment level with the pre-treatment level.

In some embodiments, the present invention provides methods of inhibiting a SAPK in a cell in an individual, the method generally involving administering to an individual in need thereof an effective amount of pirfenidone or a pirfenidone analog; comparing a second post-treatment level of SAPK activity in a biological sample from the individual to a first post-treatment level of SAPK activity; and adjusting the dose of the pirfenidone or pirfenidone analog based on the results of the comparison step. The comparison step involves detecting a second post-treatment SAPK activity level; detecting a first post-treatment SAPK activity level; and comparing the second post-treatment level with the first post-treatment level.

The present invention provides a method for treating a disorder in an individual, and a method for inhibiting a SAPK in a cell of an individual, the method generally involving comparing a post-treatment level of SAPK activity in a biological sample from an individual to a pre-treatment level of SAPK activity from an individual, wherein the post-treatment sample is from an individual who has been treated with pirfenidone or a pirfenidone analog, and wherein the pre-treatment sample is from the same individual before treatment with pirfenidone or pirfenidone analog; and adjusting the dose of the pirfenidone or pirfenidone analog based on the results of the comparison step. The comparison step involves detecting a pre-treatment SAPK activity level; detecting a post-treatment SAPK activity level; and comparing the post-treatment level with the pre-treatment level.

In some embodiments, a subject method comprises administering to an individual in need thereof an effective amount of pirfenidone or a pirfenidone analog; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog; comparing a second post-treatment level of SAPK activity in a biological sample from the individual to a first post-treatment level of SAPK activity; and adjusting the dose of the pirfenidone or pirfenidone analog based on the results of the comparison step.

The level of SAPK activity is measured in a biological sample taken from the individual. Suitable biological samples include, but are not limited to, peripheral blood mononuclear cells (PBMC). SAPK activity is in some embodiments assayed in whole, intact cells. In other embodiments, SAPK activity is measured in cell lysates. In other embodiments, SAPK activity is measured in the soluble fraction of a cell lysate. In some embodiments, SAPK is partially isolated from the sample before activity levels are assayed.

Monitoring SAPK Activity Levels

The comparison step comprises detecting a level of SAPK activity in a biological sample from an individual. Monitoring the level of a SAPK activity in a biological sample from an individual treated with pirfenidone or pirfenidone analog monotherapy or combination therapy, or from a pre-treatment individual, is accomplished by any known method. Methods of detecting SAPK activity, and measuring a level of SAPK activity, are known in the art. SAPK kinase assays are described in the literature. See, e.g., Forrer et al. (1998) *Biol. Chem.* 379:1101-1111; and U.S. Pat. No. 6,541,447. SAPK enzymatic activity is determined by measuring the level of phosphorylated SAPK substrate, e.g., a phosphorylated peptide or polypeptide substrate formed by action of a SAPK on a substrate in the presence of a phosphate source. In many embodiments, antibody specific for a phosphorylated SAPK substrate is used, e.g., antibody that specifically recognizes phosphorylated SAPK substrate, but not unphosphorylated SAPK substrate. In many assays, the level of SAPK activity correlates with the level of SAPK substrate phosphorylation, e.g., a high level of SAPK substrate phosphorylation indicates a high level of SAPK activity, and a low level of SAPK substrate phosphorylation indicates a low level of SAPK activity.

SAPK substrates are known in the art. Suitable substrates include naturally-occurring substrates; synthetic substrates (e.g., synthetic peptides); fusion proteins comprising a SAPK substrate and a fusion partner; and the like. Suitable substrates include ATF-2; CREB; myelin basic protein; and fragments, including synthetic fragments, of any naturally-occurring substrate that are capable of being phosphorylated by a SAPK; and the like. SAPK kinase substrates are in some embodiments linked to a moiety that can be detected. In some embodiments, a SAPK substrate is attached to a solid support, including, but not limited to, glass, cellulose, polyacrylamide, nylon, polystyrene, polyvinyl chloride or polypropylene.

As one non-limiting example, an enzyme-linked immunosorbent assay is used. A substrate for the SAPK is immobilized on an insoluble substrate (e.g., the wells of a microtiter plate); and the SAPK is added, in the presence of a phosphate source (e.g., ATP), for a suitable period of time and under conditions that allow phosphorylation of the substrate. The level of phosphorylation is determined using antibody specific for phosphorylated substrate. Antibody is either directly detectably labeled, or is unlabeled, and is detected using a second, labeled antibody specific for the antibody that specifically binds phosphorylated SAPK substrate.

Antibody to a phosphorylated substrate is in some embodiments detectably labeled. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In and $^{99}$Tc.

An enzyme linked immunosorbent assay (ELISA) is used in some embodiments. ELISAs generally involve coating the well of a 96 well microtiter plate with the protein being detected (e.g., phosphorylated SAPK substrate), adding a first antibody, which specifically recognizes and binds the protein, which first antibody is conjugated to a detectable compound such as an enzymatic substrate (e.g., horseradish peroxidase, luciferase, β-galactosidase, or alkaline phosphatase) to the well and incubating for a period of time, and detecting the presence of the protein.

Alternatively, the first antibody that specifically binds the substrate is not conjugated to a detectable compound; instead, a second antibody (which recognizes and binds to the antibody specific for the phosphorylated SAPK substrate) coupled (e.g., covalently linked or non-covalently linked) to a detectable compound is added to the well after allowing the first antibody to bind.

As a further alternative, instead of coating the well with the protein being detected, a first antibody specific for SAPK substrate is coated on the well. In this case, a second antibody conjugated to a detectable compound is added following the addition of the protein being detected to the first antibody-coated well. The second antibody is specific for phosphorylated SAPK substrate.

Those skilled in the art are knowledgeable regarding parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

In some embodiments, a protein blot ("Western blot") is used. Western blot analysis generally comprises preparing protein samples, electrophoresis of the protein samples in a polyacrylamide gel (e.g., 8%-20% SDS-PAGE depending on the molecular weight of the proteins), transferring the protein sample from the polyacrylamide gel to a membrane such as nitrocellulose, PVDF or nylon, blocking the membrane in blocking solution (e.g., phosphate-buffered saline (PBS) with 3% BSA (bovine serum albumin) or non-fat milk), washing the membrane in washing buffer (e.g., PBS-Tween 20™ nonionic detergent), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the proteins recognized by the primary antibody. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

In other embodiments, immunoprecipitation is used. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in sodium dodecyl sulfate (SDS)/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

One non-limiting example of a radioactive assay to measure enzymatic activity of a SAPK is as follows. In a final reaction volume of 25 µl, SAPK2a (5-10 mU) is incubated with 25 mM Tris pH 7.5, 0.02 mM EGTA, 0.33 mg/ml myelin basic protein, 10 mM magnesium acetate and [$\gamma$-$^{33}$P-ATP] (specific activity approximately 500 cpm/pmol, concentration as required). The reaction is initiated by the addition of the Mg/ATP mix. After incubation for 40 minutes at room temperature, the reaction is stopped by addition of 5 µl of a 3% phosphoric acid solution. Ten µl of the reaction is then spotted onto a P30 filtermat and washed three times for 5 minutes in 75 mM phosphoric acid and once more in methanol prior to drying and scintillation counting.

A non-limiting example of a non-radioactive assay method to measure enzymatic activity of a SAPK is an IMAP™ fluorescence polarization technique, as follows. The IMAP™ method is based on the high affinity binding of phosphate at high salt concentration by immobilized metal ($M^{III}$) coordination complexes on nanoparticles. The IMAP binding reagent comprises immobilized metal ($M^{III}$) coordination complexes on nanoparticles. When a fluorescent substrate is phosphorylated by a kinase, it can bind to the IMAP binding reagent, whose molecular size is large relative to the substrate. This gives a large increase in the polarization of the fluorescence of the substrate. The IMAP binding reagent complexes with phosphate groups on phosphopeptides generated in a kinase reaction. Such binding causes a change in the rate of molecular motion of the peptide, and results in an increase in the fluorescence polarization value observed for the fluorescein label attached at the end of the peptide. This assay can be conducted in various formats, e.g., a single vessel, a multi-well format, etc. A sample containing enzyme, substrate, and ATP (adenosine triphosphate) is incubated for 1 hour at room temperature. The IMAP™ binding reagent is added, and the fluorescence polarization is measured. (Molecular Devices' IMAP p38 assay kit; following manufacturer's instructions; Molecular Devices).

In some embodiments, SAPK activity is detected in cell lysates. For example SAPK activity is detected by pulsing whole cells with $\gamma$-$^{32}$P-ATP; making a cell lysate from the pulsed cells; processing the lysate to separate the insoluble fraction from the soluble fraction; contacting the soluble fraction with an antibody specific for phosphorylated SAPK substrate that is immobilized on an insoluble support; and measuring the amount of radioactivity bound to the immobilized antibody.

For example, PBMCs are obtained from a patient before initiation of pirfenidone or pirfenidone analog therapy ("pre-treatment PBMCs"). PBMCs are then obtained from the same patient at a time after the beginning of pirfenidone or pirfenidone analog therapy ("post-treatment PBMCs"). SAPK expression is induced in the cells (e.g., with TNF, UVC, sorbitol, and the like), and the cells are pulsed with $\gamma$-$^{32}$P-labeled ATP. Soluble protein is extracted from the cells, and SAPK substrate is separated from other soluble proteins by immunoadsorption. For example, antibody to CREB is used to immunoprecipitate or immunoadsorb SAPK substrate. Immunoadsorption can be carried out using antibody specific for phosphorylated SAPK substrate immobilized on an insoluble support. The amount of radioactivity bound to the immobilized antibody is measured. The amount of radioactivity bound to immobilized antibody from the pre-treatment and post-treatment PBMCs is compared.

Dose Titering

After the level of SAPK activity is determined, e.g., after the comparing step, the dose of pirfenidone or pirfenidone analog is adjusted ("titered") based on the results of the monitoring step, such that effective amounts of the pirfenidone or pirfenidone analog are administered to ameliorate the clinical course of disease. Thus, in some embodiments, a subject method comprises administering to an individual an effective amount of a first dosage of a pirfenidone or pirfenidone analog for a first period of time; comparing a post-treatment SAPK activity level to a pre-treatment SAPK activity level, or comparing a second post-treatment SAPK activity level to a first post-treatment SAPK activity level, where the comparison step involves detecting a SAPK activity level in a biological sample from the individual; and administering to the individual a second dosage of a pirfenidone or pirfenidone analog for a second period of time. In some embodiments, the second dosage of pirfenidone or pirfenidone analog is higher than the first dosage of pirfenidone or pirfenidone analog. In other embodiments, the second dosage of pirfenidone or pirfenidone analog is the same as the first dosage of pirfenidone or pirfenidone analog.

Typically, a SAPK activity level is measured at a first time point (e.g., before the beginning of treatment with pirfenidone or pirfenidone analog, or at any time during treatment); a SAPK activity level is measured at a second time point which is later than the first time point (e.g., after the beginning of treatment, or at any time after the first time point); and the second time point SAPK activity level is compared to the first time point SAPK activity level. A SAPK activity level measured at a first time point which is a time before the beginning of treatment with pirfenidone or pirfenidone analog is referred to as a "pre-treatment SAPK activity level." A SAPK activity level that is measured at a time point after the beginning of pirfenidone or pirfenidone analog treatment is referred to a "post-treatment SAPK activity level." Where two post-treatment SAPK activity levels are measured and compared, a SAPK activity level measured at a first post-treatment time point is referred to as a "first post-treatment SAPK activity level," and a SAPK activity level measured at a second post-treatment time point is referred to as a "second post-treatment SAPK activity level."

Comparing a Post-Treatment SAPK Activity Level to a Pre-Treatment SAPK Activity Level In some embodiments, a post-treatment SAPK activity level is compared to a pre-treatment SAPK activity level. In these embodiments, where a first dosage of pirfenidone or pirfenidone analog is administered for a first time period, and the post-treatment SAPK activity level is from about 40% to about 80% lower than the pre-treatment SAPK activity level, the dosage of pirfenidone or pirfenidone analog is not changed, e.g., where the post-treatment SAPK activity level is from about 40% to about 50%, from about 50% to about 60%, from about 60% to about 70%, or from about 70% to about 80% lower than the pre-treatment SAPK activity level, the first dosage of pirfenidone or pirfenidone analog that resulted in the decrease the SAPK activity level is maintained for at least a second time period of therapy.

Where a first dosage of pirfenidone or pirfenidone analog is administered for a first time period, and the post-treatment SAPK activity level is from about 10% to about 40% lower than the pre-treatment SAPK activity level, the dosage of pirfenidone or pirfenidone analog is increased, e.g., where the post-treatment SAPK activity level is from about 10% to about 15%, from about 15% to about 20%, from about 20% to about 25%, from about 25% to about 30%, from about 30% to about 35%, or from about 35% to about 40% lower than the pre-treatment SAPK activity level, a second dosage of pirfenidone or pirfenidone analog that is higher than the first dosage of pirfenidone or pirfenidone analog is administered for at least a second time period. For example, the second dosage of pirfenidone or pirfenidone analog is at least about 10%, at least about 20%, at least about 30%, at least about 40%, at least about 50%, at least about 60%, at least about 70%, at least about 80%, at least about 90%, at least about 2-fold, at least about 2.5-fold, at least about 3-fold, at least about 3.5-fold, or at least about 4-fold, or more, higher than the first dosage of pirfenidone or pirfenidone analog.

Where a first dosage of pirfenidone or pirfenidone analog is administered for a first time period, and the post-treatment SAPK activity level differs by less than about 10% of the pre-treatment SAPK activity level, a lack of response to the treatment may be indicated. In this case, therapy with the pirfenidone or pirfenidone analog is re-evaluated, and in some instances, discontinued.

Comparing a Second Post-Treatment SAPK Activity Level to a First Post-Treatment SAPK Activity Level In some embodiments, SAPK activity levels are measured at two or more post-treatment times to monitor the efficacy of treatment during the course of a subject therapy. In these embodiments, a second post-treatment SAPK activity level is compared to a SAPK activity level at a first post-treatment SAPK activity level.

In these embodiments, where a first dosage of pirfenidone or pirfenidone analog is administered for a first time period, and the second post-treatment SAPK activity level is from about 40% to about 80% lower than the first post-treatment SAPK activity level, the dosage of pirfenidone or pirfenidone analog is not changed, e.g., where the second post-treatment SAPK activity level is from about 40% to about 50%, from about 50% to about 60%, from about 60% to about 70%, or from about 70% to about 80% lower than the first post-treatment SAPK activity level, the first dosage of pirfenidone or pirfenidone analog that resulted in the decrease the SAPK activity level is maintained for at least a second time period of therapy.

Where a first dosage of pirfenidone or pirfenidone analog is administered for a first time period, and the second post-treatment SAPK activity level is from about 10% to about 40% lower than the first post-treatment SAPK activity level, the dosage of pirfenidone or pirfenidone analog is increased, e.g., where the second post-treatment SAPK activity level is from about 10% to about 15%, from about 15% to about 20%, from about 20% to about 25%, from about 25% to about 30%, from about 30% to about 35%, or from about 35% to about 40% lower than the first post-treatment SAPK activity level, a second dosage of pirfenidone or pirfenidone analog that is higher than the first dosage of pirfenidone or pirfenidone analog is administered for at least a second time period. For example, the second dosage of pirfenidone or pirfenidone analog is at least about 10%, at least about 20%, at least about 30%, at least about 40%, at least about 50%, at least about 60%, at least about 70%, at least about 80%, at least about 90%, at least about 2-fold, at least about 2.5-fold, at least about 3-fold, at least about 3.5-fold, or at least about 4-fold, or more, higher than the first dosage of pirfenidone or pirfenidone analog.

Combination Therapies

As discussed above, in some embodiments, a subject method involves pirfenidone or pirfenidone analog combination therapy with at least a second therapeutic agent. Suitable additional therapeutic agents include, but are not limited to, a Type I interferon receptor agonist, a Type II interferon receptor agonist, a Type III interferon receptor agonist, ribavirin, an anti-cancer agent (e.g., an anti-neoplastic agent, an anti-proliferative agent, a cytotoxic agent), an anti-angiogenic agent, an anti-inflammatory agent, an anti-fibrotic agent, a hematopoietic agent, and a non-pirfenidone TNFα antagonist.

In some embodiments, a subject method comprises administering to an individual in need thereof an effective amount of pirfenidone or a pirfenidone analog and an effective amount of a Type II interferon receptor agonist; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of IFN-γ; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of a Type I interferon receptor agonist; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of IFN-α; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of consensus IFN-α; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of INFERGEN® interferon alfacon-1; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of IFN-α 2a; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of IFN-α 2b; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of PEGylated IFN-α; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of PEGylated consensus IFN-α (CIFN); comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of PEGASYS® PEGylated IFN-α2a; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog and an effective amount of PEG-INTRON® PEGylated IFN-α2b; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog, an effective amount of a Type II interferon receptor agonist, and an effective amount of a Type I interferon receptor agonist; comparing a post-treatment level of SAPK activity in a biological sample from the individual to a pre-treatment level of SAPK activity; and adjusting the dose of the pirfenidone or pirfenidone analog based on the results of the comparison step.

In some embodiments, a subject method comprises administering to an individual in need thereof an effective amount of pirfenidone or a pirfenidone analog, an effective amount of IFN-γ, and an effective amount of an IFN-α; comparing a post-treatment level of SAPK activity in a biological sample from the individual to a pre-treatment level of SAPK activity; and adjusting the dose of the pirfenidone or pirfenidone analog based on the results of the comparison step.

In any of the above embodiments, the subject method further comprises administering an effective amount of a TNF-α antagonist. In any of the above embodiments, the subject method further comprises administering an effective amount of ribavirin.

Treatment Methods

The present invention provides methods for treating a disorder that is amenable to treatment by inhibiting a SAPK in a cell in an individual; methods of treating a viral infection; methods for treating an inflammatory disorder; methods for treating a TNF-mediated disorder; methods for treating a proliferative disorder, including angiogenesis-mediated disorders, cancer, and fibrotic disorders; and methods for inhibiting a SAPK activity in a cell in an individual.

The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

In some embodiments, the methods further involve administering an effective amount of an additional therapeutic agent, where suitable additional therapeutic agents include, but are not limited to, a Type I interferon receptor agonist, a Type II interferon receptor agonist, a Type II interferon receptor agonist, ribavirin, an anti-cancer agent (e.g., an anti-neoplastic agent, an anti-proliferative agent, a cytotoxic agent), an anti-angiogenic agent, an anti-inflammatory agent, an anti-fibrotic agent, a hematopoietic agent, and a non-pirfenidone TNFα antagonist.

Cancer Therapy

The present invention provides methods of treating cancer in an individual having a cancer. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step. In some embodiments, the methods further involve administering an effective amount of at least a second therapeutic agent, e.g., a Type I interferon receptor agonist; and/or an anti-cancer agent (e.g., an anti-neoplastic agent, and anti-proliferative agent, a cytotoxic agent).

The methods are effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, effective amounts of a therapeutic agent (e.g., pirfenidone or a pirfenidone analog; or pirfenidone or pirfenidone analog and a second therapeutic agent) are amounts that, in monotherapy or combination therapy, are sufficient to reduce tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be the tumor load present in a genetically identical animal lot treated with the pirfenidone or pirfenidone analog monotherapy or combination therapy. In non-experimental systems, a suitable control may be the tumor load present before administering the pirfenidone or pirfenidone analog monotherapy or combination therapy. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood; and the like.

The methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, effective amounts of a therapeutic agent (e.g., pirfenidone or a pirfenidone analog; or pirfenidone or pirfenidone analog and a second therapeutic agent) are amounts that, in monotherapy or combination therapy, are sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be the growth rate of a tumor in a genetically identical animal not treated with pirfenidone or pirfenidone analog monotherapy or combination therapy. In non-experimental systems, a suitable control may be the growth rate of a tumor observed before administering the pirfenidone or pirfenidone analog monotherapy or combination therapy. Other suitable controls may be a placebo control.

Whether growth of a tumor is inhibited can be determined using any known method, including, but not limited to, an in vitro proliferation assay such as a $^3$H-thymidine uptake assay, and the like.

The methods of the invention are useful for treating a wide variety of cancers, including carcinomas, sarcomas, leukemias, and lymphomas.

Carcinomas that can be treated using the methods of the invention include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be treated using a method of the invention include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; and the like.

Treatment of Fibrotic Disorders

The present invention further provides methods of therapeutically treating a fibrotic disorder such as fibrosis of the lung, kidney, liver, heart, and the like in individuals who present with clinical signs of fibrotic disorder to reduce risk of death and to improve clinical functions. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step. In some embodiments, a subject method further comprises administering at least a second therapeutic agent, e.g., a Type I interferon receptor agonist; a Type II interferon receptor agonist; a non-pirfenidone TNF-α antagonist; an anti-fibrotic agent; and the like.

Fibrosis is generally characterized by the pathologic or excessive accumulation of collagenous connective tissue. Fibrotic disorders include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport's syndrome, HIV-associated nephropathy, polycystic kidney disease, Fabry's disease, diabetic nephropathy, chronic glomerulonephritis, nephritis associated with systemic lupus, and the like), cutis keloid formation, progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's opthalmopathy, diabetic retinopathy, glaucoma, Peyronie's disease, penis fibrosis, urethrostenosis after the test using a cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), fibrosis induced by chemical or environmental insult (e.g., cancer chemotherapy, pesticides, radiation (e.g., cancer radiotherapy), and the like), and the like.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, when administered to an individual having a fibrotic disorder, are effective to reduce fibrosis or reduce the rate of progression of fibrosis by at least about 10%, at least about 15%, at least about 20%, at least about 25%, at least about 30%, at least about 35%, at least about 40%, at least about 45%, or at least about 50%, or more, compared with the degree of fibrosis in the individual prior to treatment or compared to the rate of progression of fibrosis that would have been experienced by the patient in the absence of the pirfenidone or pirfenidone analog monotherapy or combination therapy.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, when administered to an individual having a fibrotic disorder, are effective to increase, or to reduce the rate of deterioration of, at least one function of the organ affected by fibrosis (e.g., lung, liver, kidney, etc.) by at least about 10%, at least about 15%, at least about 20%, at least about 25%, at least about 30%, at least about 35%, at least about 40%, at least about 45%, or at least about 50%, or more, compared to the basal level of organ function in the individual prior to a subject monotherapy or combination therapy or compared to the rate of deterioration in organ function that would have been experienced by the individual in the absence of the subject monotherapy or combination therapy.

Methods of measuring the extent of fibrosis in a given organ, and methods of measuring the function of any given organ, are well known in the art.

A subject combination therapy is effective in reducing clinical symptoms, reducing morbidity or mortality, or reducing risk of death. These clinical outcomes are readily determined by those skilled in the art. Clinical outcome parameters for fibrotic disorders are readily measured by known assays.

Idiopathic Pulmonary Fibrosis

The present invention provides methods of treating idiopathic pulmonary fibrosis (IPF). The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

In some embodiments, a diagnosis of IPF is confirmed by the finding of usual interstitial pneumonia (UIP) on histopathological evaluation of lung tissue obtained by surgical biopsy. The criteria for a diagnosis of IPF are known. Ryu et al. (1998) *Mayo Clin. Proc.* 73:1085-1101.

In other embodiments, a diagnosis of IPF is a definite or probable IPF made by high resolution computer tomography (HRCT). In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, is effective to decrease disease progression by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or more, compared with a placebo control or an untreated control.

Disease progression is the occurrence of one or more of the following: (1) a decrease in predicted FVC of 10% or more; (2) an increase in A-a gradient of 5 mm Hg or more; (3) a decrease of 15% or more in single breath $DL_{co}$. Whether disease progression has occurred is determined by measuring one or more of these parameters on two consecutive occasions 4 to 14 weeks apart, and comparing the value to baseline.

Thus, e.g., where an untreated or placebo-treated individual exhibits a 50% decrease in FVC over a period of time, an individual administered with an effective amount of pirfenidone or pirfenidone analog exhibits a decrease in FVC of 45%, about 42%, about 40%, about 37%, about 35%, about 32%, about 30%, or less, over the same time period.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, are effective to increase progression-free survival time, e.g., the time from baseline (e.g., a time point from 1 day to 28 days before beginning of treatment) to death or disease progression is increased by at least about 10%, at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared a placebo-treated or an untreated control individual. Thus, e.g., in some embodiments effective amounts are any dosages that is effective to increase the progression-free survival time by at least about 1 week, at least about 2 weeks, at least about 3 weeks, at least about 4 weeks, at least about 2 months, at least about 3 months, at least about 4 months, at least about 5 months, at least about 6 months, at least about 8 months, at least about 10 months, at least about 12 months, at least about 18 months, at least about 2 years, at least about 3 years, or longer, compared to a placebo-treated or untreated control.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, are effective to increase at least one parameter of lung function, e.g., an effective amount of a pirfenidone or pirfenidone analog is any dosage that increases at least one parameter of lung function by at least about 10%, at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared to an untreated individual or a placebo-treated control individual. In some of these embodiments, a determination of whether a parameter of lung function is increased is made by comparing the baseline value with the value at any time point after the beginning of treatment, e.g., 48 weeks after the beginning of treatment, or between two time points, e.g., about 4 to about 14 weeks apart, after the beginning of treatment.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, are effective to increase the FVC by at least about 10% at least about 20%, at least about 25%, at least about 30%, at least about 40%, at least about 50%, at least about 60%, at least about 70%, at least about 80%, at least about 90%, at least about 2-fold, at least about 3-fold, at least about 4-fold, at least about 5-fold, or more compared to baseline on two consecutive occasions 4 to 14 weeks apart.

In some of these embodiments, effective amounts of a therapeutic agent (e.g., pirfenidone or a pirfenidone analog; or pirfenidone or pirfenidone analog and a second therapeutic agent) are amounts that, in monotherapy or combination therapy, results in a decrease in alveolar:arterial (A-a) gradient of at least about 5 mm. Hg, at least about 7 mm Hg, at least about 10 mm Hg, at least about 12 mm Hg, at least about 15 mm Hg, or more, compared to baseline.

In some of these embodiments, effective amounts of a therapeutic agent (e.g., pirfenidone or a pirfenidone analog; or pirfenidone or pirfenidone analog and a second therapeutic agent) are amounts that, in monotherapy or combination therapy, increases the single breath $DL_{co}$ by at least about 15%, at least about 20%, at least about 30%, at least about 40%, at least about 50%, at least about 60%, at least about 70%, at least about 80%, at least about 90%, at least about 2-fold, at least about 3-fold, at least about 4-fold, at least about 5-fold, or more, compared to baseline. $CL_{co}$ is the lung diffusing capacity for carbon monoxide, and is expressed as mL CO/mm Hg/second.

Parameters of lung function include, but are not limited to, forced vital capacity (FVC); forced expiratory volume ($FEV_1$); total lung capacity; partial pressure of arterial oxygen at rest; partial pressure of arterial oxygen at maximal exertion.

Lung function can be measured using any known method, including, but not limited to spirometry.

Liver Fibrosis

The present invention provides methods of treating liver fibrosis, including reducing clinical liver fibrosis, reducing the likelihood that liver fibrosis will occur, and reducing a parameter associated with liver fibrosis. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step. Of particular interest in many embodiments is treatment of humans.

Liver fibrosis is a precursor to the complications associated with liver cirrhosis, such as portal hypertension, progressive liver insufficiency, and hepatocellular carcinoma. A reduction in liver fibrosis thus reduces the incidence of such complications. Accordingly, the present invention further provides methods of reducing the likelihood that an individual will develop complications associated with cirrhosis of the liver.

As used herein, effective amounts of a therapeutic agent (e.g., pirfenidone or a pirfenidone analog; or pirfenidone or pirfenidone analog and a second therapeutic agent) are amounts that, in monotherapy or combination therapy, is effective in reducing liver fibrosis or reduce the rate of progression of liver fibrosis; and/or that is effective in reducing the likelihood that an individual will develop liver fibrosis; and/or that is effective in reducing a parameter associated with liver fibrosis; and/or that is effective in reducing a disorder associated with cirrhosis of the liver.

The invention also provides a method for treatment of liver fibrosis in an individual comprising administering to the individual an amount of pirfenidone or pirfenidone analog that is effective for prophylaxis or therapy of liver fibrosis in the individual, e.g., increasing the probability of survival, reducing the risk of death, ameliorating the disease burden or slowing the progression of disease in the individual.

Whether treatment with pirfenidone or pirfenidone analog in monotherapy or combination therapy is effective in reducing liver fibrosis can be determined by any of a number of well-established techniques for measuring liver fibrosis and liver function. Whether liver fibrosis is reduced is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) *Hepatol* 31:241-246; and METAVIR (1994) *Hepatology* 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) *Hepatol.* 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) *J. Hepatol.* 13:372.

The Ishak scoring system is described in Ishak (1995) *J. Hepatol.* 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, effects a change of one unit or more in the fibrosis stage based on pre- and post-therapy liver biopsies. In particular embodiments, a therapeutically effective amount of pirfenidone or pirfenidone analog reduce liver fibrosis by at least one unit in the METAVIR, the Knodell, the Scheuer, the Ludwig, or the Ishak scoring system.

Secondary, or indirect, indices of liver function can also be used to evaluate the efficacy of treatment with a subject combination therapy. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

In another embodiment, effective amounts of a therapeutic agent (e.g., pirfenidone or a pirfenidone analog; or pirfenidone or pirfenidone analog and a second therapeutic agent) are amounts that, in monotherapy or combination therapy, are effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or in a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

In another embodiment, effective amounts of a therapeutic agent (e.g., pirfenidone or a pirfenidone analog; or pirfenidone or pirfenidone analog and a second therapeutic agent) are amounts that, in monotherapy or combination therapy, are effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or in a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with a subject therapy. These include: indocyanine green clearance (ICG), galactose elimination capacity (GEC), aminopyrine breath test (ABT), antipyrine clearance, monoethylglycine-xylidide (MG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but is not limited to, development of ascites, variceal bleeding, portal hypertension, jaundice, progressive liver insufficiency, encephalopathy, hepatocellular carcinoma, liver failure requiring liver transplantation, and liver-related mortality.

In another embodiment, effective amounts of a therapeutic agent (e.g., pirfenidone or a pirfenidone analog; or pirfenidone or pirfenidone analog and a second therapeutic agent) are amounts that, in monotherapy or combination therapy, are effective in reducing the incidence of (e.g., the likelihood that an individual will develop) a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or in a placebo-treated individual.

Whether a subject monotherapy or combination therapy is effective in reducing the incidence of a disorder associated with cirrhosis of the liver can readily be determined by those skilled in the art.

Reduction in liver fibrosis increases liver function. Thus, the invention provides methods for increasing liver function, generally involving administering therapeutically effective amounts of pirfenidone or pirfenidone analog. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal range of alanine transaminase is from about 7 to about 56 units per liter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

In another embodiment, effective amounts of a therapeutic agent (e.g., pirfenidone or a pirfenidone analog; or pirfenidone or pirfenidone analog and a second therapeutic agent) are amounts that, in monotherapy or combination therapy, are effective to increase liver function by at least about 10%, at least about 20%, at least about 30%, at least about 40%, at least about 50%, at least about 60%, at least about 70%, at least about 80%, or more. For example, effective amounts of a therapeutic agent (e.g., pirfenidone or a pirfenidone analog; or pirfenidone or pirfenidone analog and a second therapeutic agent) are amounts that, in monotherapy or combination therapy, are effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. Effective amounts of a therapeutic agent (e.g., pirfenidone or a pirfenidone analog; or pirfenidone or pirfenidone analog and a second therapeutic agent) are also amounts that, in monotherapy or combination therapy, increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Renal Fibrosis

Renal fibrosis is characterized by the excessive accumulation of extracellular matrix (ECM) components. Overproduction of transforming growth factor-beta (TGF-β) is believed to underlie tissue fibrosis caused by excess deposition of ECM, resulting in disease. TGF-β's fibrogenic action results from simultaneous stimulation of matrix protein synthesis, inhibition of matrix degradation and enhanced integrin expression that facilitates ECM assembly.

The present invention provides methods of treating renal fibrosis. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

As used herein, an "effective amount" a therapeutic agent is any dosage that is effective in reducing renal fibrosis; and/or that is effective in reducing the likelihood that an individual will develop renal fibrosis; and/or that is effective in reducing a parameter associated with renal fibrosis; and/or that is effective in reducing a disorder associated with fibrosis of the kidney.

In one embodiment, effective amounts of a therapeutic agent (e.g., pirfenidone or a pirfenidone analog; or pirfenidone or pirfenidone analog and a second therapeutic agent) are amounts that, in monotherapy or combination therapy, are sufficient to reduce renal fibrosis, or reduce the rate of progression of renal fibrosis, by at least about 10%, at least about 15%, at least about 20%, at least about 25%, at least about 30%, at least about 35%, at least about 40%, at least about 45%, at least about 50%, compared to the degree of renal fibrosis in the individual prior to treatment, or compared to the rate of progression of renal fibrosis that would have been experienced by the patient in the absence of treatment.

Whether fibrosis is reduced in the kidney is determined using any known method. For example, histochemical analysis of kidney biopsy samples for the extent of ECM deposition and/or fibrosis is performed. Other methods are known in the art. See, e.g., Masseroli et al. (1998) *Lab. Invest.* 78:511-522; U.S. Pat. No. 6,214,542.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, are effective to increase kidney function by at least about 10%, at least about 15%, at least about 20%, at least about 25%, at least about 30%, at least about 35%, at least about 40%, at least about 45%, at least about 50%, compared to the basal level of kidney function in the individual prior to treatment.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, are effective to slow the decline in kidney function by at least about 10%, at least about 15%, at least about 20%, at least about 25%, at least about 30%, at least about 35%, at least about 40%, at least about 45%, at least about 50%, compared to the decline in kidney function that would occur in the absence of treatment.

Kidney function can be measured using any known assay, including, but not limited to, plasma creatinine level (where normal levels are generally in a range of from about 0.6 to about 1.2 mg/dL); creatinine clearance (where the normal range for creatinine clearance is from about 97 to about 137 mL/minute in men, and from about 88 to about 128 mL/minute in women); the glomerular filtration rate (either calculated or obtained from inulin clearance or other methods), blood urea nitrogen (where the normal range is from about 7 to about 20 mg/dL); and urine protein levels.

Treatment of Angiogenesis-Mediated Disorders

The present invention provides methods for treating angiogenic disorders. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

In a subject method of treating an angiogenic disorder, effective amounts of a therapeutic agent (e.g., pirfenidone or a pirfenidone analog; or pirfenidone or pirfenidone analog and a second therapeutic agent) are amounts that, in monotherapy or combination therapy, are angiostatic, e.g., an amount that reduces angiogenesis by at least about 10%, at least about 20%, at least about 25%, at least about 30%, at least about 40%, at least about 50%, at least about 60%, at least about 70%, at least about 80%, or at least about 90%, or more, compared with the level of angiogenesis in the absence of treatment with the subject monotherapy or combination therapy.

Many systems are available for assessing angiogenesis. For example, as angiogenesis is required for solid tumor growth, the inhibition of tumor growth in an animal model may be used as an index of the inhibition of angiogenesis. Angiogenesis may also be assessed in terms of models of wound-healing, in cutaneous or organ wound repair; and in chronic inflammation, e.g., in diseases such as rheumatoid arthritis, atherosclerosis and idiopathic pulmonary fibrosis (IPF). It may also be assessed by counting vessels in tissue sections, e.g., following staining for marker molecules, e.g., CD3H, Factor VIII or PECAM-1.

Whether angiogenesis is reduced can be determined using any method known in the art, including, e.g., stimulation of neovascularization into implants impregnated with relaxin; stimulation of blood vessel growth in the cornea or anterior eye chamber; stimulation of endothelial cell proliferation, migration or tube formation in vitro; and the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

A system in widespread use for assessing angiogenesis is the corneal micropocket assay of neovascularization, as may be practiced using rat corneas. This in vivo model is widely accepted as being generally predictive of clinical usefulness. See, e.g., O'Reilly et. al. (1994) *Cell* 79:315-328, Li et. al. (1991) *Invest. Ophthalmol. Vis. Sci.* 32(11):2898-905; and Miller et. al. (1994) *Am. J. Pathol.* 145(3):574-84.

A subject method is useful for treating angiogenic disorders, e.g., any disease characterized by pathological neovascularization. Such disorders include, but are not limited to, solid tumors, hemangiomas, rheumatoid arthritis, atherosclerosis, fibrotic disorders, including idiopathic pulmonary fibrosis (IPF), liver fibrosis, and renal fibrosis; but also include BPH, vascular restenosis, arteriovenous malformations (AVM), retinopathies, including diabetic retinopathy, meningioma, hemangiomas, thyroid hyperplasias (including Grave's disease), neovascular glaucoma, neovascularization associated with corneal injury, neovascularization associated with corneal transplantation, neovascularization associated with corneal graft, psoriasis, angiofibroma, hemophilic joints, hypertrophic scars, osler-weber syndrome, age-related macular degeneration, pyogenic granuloma retrolental fibroplasia, scleroderma, trachoma, vascular adhesions, synovitis, dermatitis, an inflammatory bowel disease such as, for example, Crohn's disease or ulcerative colitis, and endometriosis.

Viral Infections

The present invention provides methods of treating a virus infection, and methods of reducing viral load, or reducing the time to viral clearance, or reducing morbidity or mortality in the clinical outcomes, in patients suffering from a virus infection. The present invention further provides methods of reducing the risk that an individual will develop a pathological viral infection that has clinical sequelae.

The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

In some embodiments, a subject method further comprises administering at least a second therapeutic agent, e.g. a Type I interferon receptor agonist, a Type II interferon receptor agonist, ribavirin, and the like. In some embodiments, a subject combination therapy comprises administering pirfenidone or a pirfenidone analog in combination therapy with a Type II interferon receptor agonist. In some embodiments, a subject combination therapy comprises administering pirfenidone or a pirfenidone analog in combination therapy with a Type I interferon receptor agonist. In some embodiments, a subject combination therapy comprises administering pirfenidone or a pirfenidone analog in combination therapy with a Type II interferon receptor agonist and a Type I interferon receptor agonist. In any of these embodiments, a subject combination therapy further comprises administering ribavirin.

The present invention further provides methods of therapeutically treating a virus infection in individual who present with clinical signs of viral infection following known or suspected exposure to virus. Individuals who have been in close contact with an individual who has been diagnosed with a viral infection are considered eligible for treatment with the methods of the present invention. An advantage of the subject methods is that the severity of the viral infection is reduced, e.g., the viral load is reduced, and/or the time to viral clearance is reduced, and/or the morbidity or mortality is reduced.

The present invention provides methods of prophylactically treating a viral infection in an individual who is not yet infected with a virus and/or who does not exhibit symptoms typical of a viral infection. An advantage of the present invention is that the risk that the individual will develop a pathological viral infection is reduced.

Where a subject treatment method is prophylactic, the methods reduce the risk that an individual will develop pathological infection with a virus. Effective amounts of a therapeutic agent (e.g., pirfenidone or a pirfenidone analog; or pirfenidone or pirfenidone analog and a second therapeutic agent) are amounts that, in monotherapy or combination therapy, reduce the risk or reducing the probability that an individual will develop a pathological infection with a virus. For example, an effective amount reduces the risk that an individual will develop a pathological infection by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing a pathological infection with the virus in the absence of interferon treatment.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, reduce viral load by at least about 10%, at least about 20%, at least about 25%, at least about 30%, at least about 35%, at least about 40%, at least about 50%, at least about 60%, at least about 70%, at least about 80%, at least about 90%, or more, compared to the viral load in the absence of treatment.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, reduce the time to viral clearance, by at least about 10%, at least about 20%, at least about 25%, at least about 30%, at least about 35%, at least about 40%, at least about 50%, at least about 60%, at least about 70%, at least about 80%, at least about 90%, or more, compared to the time to viral clearance in the absence of treatment.

In some embodiments, effective amounts of a therapeutic agent (e.g., pirfenidone or a pirfenidone analog; or pirfenidone or pirfenidone analog and a second therapeutic agent) are amounts that, in monotherapy or combination therapy, reduce morbidity or mortality due to a virus infection by at least about 10%, at least about 20%, at least about 25%, at least about 30%, at least about 35%, at least about 40%, at least about 50%, at least about 60%, at least about 70%, at least about 80%, at least about 90%, or more, compared to the morbidity or mortality in the absence of treatment.

Whether a subject treatment method is effective in reducing the risk of a pathological virus infection, reducing viral load, reducing time to viral clearance, or reducing morbidity or mortality due to a virus infection is readily determined by those skilled in the art. Viral load is readily measured by measuring the titer or level of virus in serum. The number of virus in the serum can be determined using any known assay, including, e.g., a quantitative polymerase chain reaction assay using oligonucleotide primers specific for the virus being assayed. Whether morbidity is reduced can be determined by measuring any symptom associated with a virus infection, including, e.g., fever, respiratory symptoms (e.g., cough, ease or difficulty of breathing, and the like.

TNF-Mediated Disorders

The present invention further provides methods of treating TNF-mediated disorders. The methods generally involve administering to an individual in need thereof an amount of a pirfenidone or pirfenidone analog; comparing a post-treatment SAPK activity level in a biological sample from the individual with a pre-treatment SAPK activity level in a biological sample from the individual and/or comparing a second post-treatment SAPK activity level in a biological sample from the individual with a first post-treatment SAPK activity level in a biological sample from the individual; and adjusting the dose of the pirfenidone or pirfenidone analog based on the results of the comparison step.

The term "TNF-mediated disorder" includes, but is not limited to, nervous system syndromes, such as relapsing-remitting, multiple sclerosis, primary and secondary multiple sclerosis, spinal multiple sclerosis, cerebral malaria, viral or bacterial infections of the central nervous system, bacterial meningitis, "autoimmune" disorders of the central nervous system, central nervous system stroke and infarction, brain edema, Parkinson's syndrome, amyotrophic lateral sclerosis, brain concussion or contusion, musculo-skeletal syndrome, such as rheumatoid arthritis, trauma-induced arthritis, arthritis caused by a microbial infection, or by a parasite, tendonitis, arthritis induced by medical products or drugs (including, small synthetic molecules as well as purified natural or synthesized peptides or proteins), pulmonary syndromes, such as acute adult respiratory distress syndrome, asthma, allergic rhinitis, allergic generalized reactions, allergic conjunctivitis, chronic obstructive pulmonary disease, and lung sarcoidosis, systemic immunologic, inflammatory, or toxic syndromes, such as endotoxemia shock syndrome, septic shock, graft-host disease following, bone-marrow transplantation, hemorrhagic shock, reperfusion injury of the brain or myocardium, thermal burns, radiation injury, general or dermal traumatic or contusion injuries, eosinophilic granuloma, diabetes mellitus (Type 2), and systemic lupus erythromatosus, and gastrointestinal syndromes, such as Crohn's disease, ulcerative colitis, and liver inflammatory disorders.

Type I Interferon Receptor Agonists

Type I interferon receptor agonists can be used to augment the combination therapies of the invention. Type I interferon receptor agonists include an IFN-α; an IFN-β; an IFN-tau; an IFN-ω; antibody agonists specific for a Type I interferon receptor; and any other agonist of Type I interferon receptor, including non-polypeptide agonists.

Interferon-Alpha

Any known IFN-α can be used in the instant invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon Tradename.

The term "IFN-α" also encompasses consensus IFN-α. Consensus IFN-α (also referred to as "CIFN" and "IFN-con" and "consensus interferon") encompasses but is not limited to the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. Use of CIFN is of particular interest.

Also suitable for use in the present invention are fusion polypeptides comprising an IFN-α and a heterologous polypeptide. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303: 540-548). Also suitable for use in the present invention are gene-shuffled forms of IFN-α. See, e.g., Masci et al. (2003) *Curr. Oncol. Rep.* 5:108-113.

PEGylated Interferon-Alpha

The term "IFN-α" also encompasses derivatives of IFN-α that are derivatized (e.g., are chemically modified) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

Any of the above-mentioned IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In some embodiments, the PEGylated IFN-α contains a PEG moiety on only one amino acid. In other embodiments, the PEGylated IFN-α contains a PEG moiety on two or more amino acids, e.g., the IFN-α contains a PEG moiety attached to two, three, four, five, six, seven, eight, nine, or ten different amino acid residues.

IFN-α may be coupled directly to PEG (i.e., without a linking group) through an amino group, a sulfhydryl group, a hydroxyl group, or a carboxyl group.

In some embodiments, the PEGylated IFN-α is PEGylated at or near the amino terminus N-terminus) of the IFN-α polypeptide, e.g., the PEG moiety is conjugated to the IFN-α polypeptide at one or more amino acid residues from amino acid 1 through amino acid 4, or from amino acid 5 through about 10.

In other embodiments, the PEGylated IFN-α is PEGylated at one or more amino acid residues from about 10 to about 28.

In other embodiments, the PEGylated IFN-α is PEGylated at or near the carboxyl terminus (C-terminus) of the IFN-α polypeptide, e.g., at one or more residues from amino acids 156-166, or from amino acids 150 to 155.

In other embodiments, the PEGylated IFN-α is PEGylated at one or more amino acid residues at one or more residues from amino acids 100-114.

The polyethylene glycol derivatization of amino acid residues at or near the receptor-binding and/or active site domains of the IFN-α protein can disrupt the functioning of these domains. In certain embodiments of the invention, amino acids at which PEGylation is to be avoided include amino acid residues from amino acid 30 to amino acid 40; and amino acid residues from amino acid 113 to amino acid 149.

In some embodiments, PEG is attached to IFN-α via a linking group. The linking group is any biocompatible linking group, where "biocompatible" indicates that the compound or group is non-toxic and may be utilized in vitro or in vivo without causing injury, sickness, disease, or death. PEG can be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

Methods for making succinimidyl propionate (SPA) and succinimidyl butanoate (SBA) ester-activated PEGs are described in U.S. Pat. No. 5,672,662 (Harris, et al.) and WO 97/03106.

Methods for attaching a PEG to an IFN-α polypeptide are known in the art, and any known method can be used. See, for example, by Park et al, Anticancer Res., 1:373-376 (1981); Zaplipsky and Lee, Polyethylene Glycol Chemistry: Biotechnical and Biomedical Applications, J. M. Harris, ed., Plenum Press, NY, Chapter 21 (1992); U.S. Pat. No. 5,985,265; U.S. Pat. No. 5,672,662 (Harris, et al.) and WO 97/03106.

Pegylated IFN-α, and methods for making same, is discussed in, e.g., U.S. Pat. Nos. 5,382,657; 5,981,709; 5,985, 265; and 5,951,974. Pegylated IFN-α encompasses conjugates of PEG and any of the above-described IFN-α molecules, including, but not limited to, PEG conjugated to interferon alpha-2a (Roferon, Hoffman LaRoche, Nutley, N.J.), where PEGylated Roferon is known as Pegasys (Hoffman LaRoche); interferon alpha 2b (Intron, Schering-Plough, Madison, N.J.), where PEGylated Intron is known as PEG-Intron (Schering-Plough); interferon alpha-2c (Berofor Alpha, Boehringer Ingelheim, Ingelheim, Germany); and consensus interferon (CIFN) as defined by determination of a consensus sequence of naturally occurring interferon alphas (Infergen®, InterMune, Inc., Brisbane, Calif.), where PEGylated Infergen is referred to as PEG-Infergen.

In many embodiments, the PEG is a monomethoxyPEG molecule that reacts with primary amine groups on the IFN-α polypeptide. Methods of modifying polypeptides with monomethoxy PEG via reductive alkylation are known in the art. See, e.g., Chamow et al. (1994) *Bioconj. Chem.* 5:133-140.

In one non-limiting example, PEG is linked to IFN-α via an SPA linking group. SPA esters of PEG, and methods for making same, are described in U.S. Pat. No. 5,672,662. SPA linkages provide for linkage to free amine groups on the IFN-α polypeptide.

For example, a PEG molecule is covalently attached via a linkage that comprises an amide bond between a propionyl group of the PEG moiety and the epsilon amino group of a surface-exposed lysine residue in the IFN-α polypeptide. Such a bond can be formed, e.g., by condensation of an α-methoxy, omega propanoic acid activated ester of PEG (mPEGspa).

As one non-limiting example, one monopegylated CIFN conjugate preferred for use herein has a linear PEG moiety of about 30 kD attached via a covalent linkage to the CIFN polypeptide, where the covalent linkage is an amide bond between a propionyl group of the PEG moiety and the epsilon amino group of a surface-exposed lysine residue in the CIFN polypeptide, where the surface-exposed lysine residue is chosen from $lys^{31}$, $lys^{50}$, $lys^{71}$, $lys^{84}$, $lys^{121}$, $lys^{122}$, $lys^{134}$, $lys^{135}$, and $lys^{165}$, and the amide bond is formed by condensation of an α-methoxy, omega propanoic acid activated ester of PEG.

Polyethylene Glycol

Polyethylene glycol suitable for conjugation to an IFN-α polypeptide is soluble in water at room temperature, and has the general formula R(O—$CH_2$—$CH_2$)$_n$O—R, where R is hydrogen or a protective group such as an alkyl or an alkanol group, and where n is an integer from 1 to 1000. Where R is a protective group, it generally has from 1 to 8 carbons.

In many embodiments, PEG has at least one hydroxyl group, e.g., a terminal hydroxyl group, which hydroxyl group is modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

In other embodiments, PEG is derivatized so that it is reactive with free carboxyl groups in the IFN-α polypeptide, e.g., the free carboxyl group at the carboxyl terminus of the IFN-α polypeptide. Suitable derivatives of PEG that are reactive with the free carboxyl group at the carboxyl-terminus of IFN-α include, but are not limited to PEG-amine, and hydrazine derivatives of PEG (e.g., PEG-NH—$NH_2$).

In other embodiments, PEG is derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the ε-amino groups in lysine residues are protonated and remain non-nucleophilic. On the other hand, reactions under suitable pH conditions may make some of the accessible lysine residues to react with selectivity.

In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-$NH_2$ groups of lysine may also react.

The PEG can be conjugated directly to the IFN-α polypeptide, or through a linker. In some embodiments, a linker is added to the IFN-α polypeptide, forming a linker-modified IFN-α polypeptide. Such linkers provide various functionalities, e.g., reactive groups such sulfhydryl, amino, or carboxyl groups to couple a PEG reagent to the linker-modified IFN-α polypeptide.

In some embodiments, the PEG conjugated to the IFN-α polypeptide is linear. In other embodiments, the PEG conjugated to the IFN-α polypeptide is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG having a molecular weight in a range of from about 2 kDa to about 100 kDa, is generally used, where the term "about," in the context of PEG, indicates that in preparations of polyethylene glycol, some molecules will weigh more, some less, than the stated molecular weight. For example, PEG suitable for conjugation to IFN-α has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

Preparing PEG-IFN-α Conjugates

As discussed above, the PEG moiety can be attached, directly or via a linker, to an amino acid residue at or near the N-terminus, internally, or at or near the C-terminus of the IFN-α polypeptide. Conjugation can be carried out in solution or in the solid phase.

N-Terminal Linkage

Methods for attaching a PEG moiety to an amino acid residue at or near the N-terminus of an IFN-α polypeptide are known in the art. See, e.g., U.S. Pat. No. 5,985,265.

In some embodiments, known methods for selectively obtaining an N-terminally chemically modified IFN-α are used. For example, a method of protein modification by reductive alkylation which exploits differential reactivity of different types of primary amino groups (lysine versus the N-terminus) available for derivatization in a particular protein can be used. Under the appropriate reaction conditions, substantially selective derivatization of the protein at the N-terminus with a carbonyl group containing polymer is achieved. The reaction is performed at pH which allows one to take advantage of the $pK_a$ differences between the ε-amino groups of the lysine residues and that of the α-amino group of the N-terminal residue of the protein. By such selective derivatization attachment of a PEG moiety to the IFN-α is controlled: the conjugation with the polymer takes place predominantly at the N-terminus of the IFN-α and no significant modification of other reactive groups, such as the lysine side chain amino groups, occurs.

C-Terminal Linkage

N-terminal-specific coupling procedures such as described in U.S. Pat. No. 5,985,265 provide predominantly monoPEGylated products. However, the purification procedures aimed at removing the excess reagents and minor multiply PEGylated products remove the N-terminal blocked polypeptides. In terms of therapy, such processes lead to significant increases in manufacturing costs. For example, examination of the structure of the well-characterized Infergen® Alfacon-1 CIFN polypeptide amino acid sequence reveals that the clipping is approximate 5% at the carboxyl terminus and thus there is only one major C-terminal sequence. Thus, in some embodiments, N-terminally PEGylated IFN-α is not used; instead, the IFN-α polypeptide is C-terminally PEGylated.

An effective synthetic as well as therapeutic approach to obtain mono PEGylated Infergen product is therefore envisioned as follows:

A PEG reagent that is selective for the C-terminal can be prepared with or without spacers. For example, polyethylene glycol modified as methyl ether at one end and having an amino function at the other end may be used as the starting material.

Preparing or obtaining a water-soluble carbodiimide as the condensing agent can be carried out. Coupling IFN-α (e.g., Infergen® Alfacon-1 CIFN or consensus interferon) with a water-soluble carbodiimide as the condensing reagent is generally carried out in aqueous medium with a suitable buffer system at an optimal pH to effect the amide linkage. A high molecular weight PEG can be added to the protein covalently to increase the molecular weight.

The reagents selected will depend on process optimization studies. A non-limiting example of a suitable reagent is EDAC or 1-ethyl-3-(3-dimethylaminopropyl)carbodiimide. The water solubility of EDAC allows for direct addition to a reaction without the need for prior organic solvent dissolution. Excess reagent and the isourea formed as the by-product of the cross-linking reaction are both water-soluble and may easily be removed by dialysis or gel filtration. A concentrated solution of EDAC in water is prepared to facilitate the addition of a small molar amount to the reaction. The stock solution is prepared and used immediately in view of the water labile nature of the reagent. Most of the synthetic protocols in literature suggest the optimal reaction medium to be in pH range between 4.7 and 6.0. However the condensation reactions do proceed without significant losses in yields up to pH 7.5. Water may be used as solvent. In view of the contemplated use of Infergen, preferably the medium will be 2-(N-morpholino)ethane sulfonic acid buffer pre-titrated to pH between 4.7 and 6.0. However, 0.1M phosphate in the pH 7-7.5 may also be used in view of the fact that the product is in the same buffer. The ratios of PEG amine to the IFN-α molecule is optimized such that the C-terminal carboxyl residue(s) are selectively PEGylated to yield monoPEGylated derivative(s).

Even though the use of PEG amine has been mentioned above by name or structure, such derivatives are meant to be exemplary only, and other groups such as hydrazine derivatives as in PEG-NH—NH$_2$ which will also condense with the carboxyl group of the IFN-α protein, can also be used. In addition to aqueous phase, the reactions can also be conducted on solid phase. Polyethylene glycol can be selected from list of compounds of molecular weight ranging from 300-40000. The choice of the various polyethylene glycols will also be dictated by the coupling efficiency and the biological performance of the purified derivative in vitro and in vivo i.e., circulation times, anti viral activities etc.

Additionally, suitable spacers can be added to the C-terminal of the protein. The spacers may have reactive groups such as SH, NH$_2$ or COOH to couple with appropriate PEG reagent to provide the high molecular weight IFN-α derivatives. A combined solid/solution phase methodology can be devised for the preparation of C-terminal pegylated interferons. For example, the C-terminus of IFN-α is extended on a solid phase using a Gly-Gly-Cys-NH$_2$ spacer and then monopegylated in solution using activated dithiopyridyl-PEG reagent of appropriate molecular weights. Since the coupling at the C-terminus is independent of the blocking at the N-terminus, the envisioned processes and products will be beneficial with respect to cost (a third of the protein is not wasted as in N-terminal PEGylation methods) and contribute to the economy of the therapy to treat chronic hepatitis C infections, liver fibrosis etc.

There may be a more reactive carboxyl group of amino acid residues elsewhere in the molecule to react with the PEG reagent and lead to monoPEGylation at that site or lead to multiple PEGylations in addition to the —COOH group at the C-terminus of the IFN-α. It is envisioned that these reactions will be minimal at best owing to the steric freedom at the C-terminal end of the molecule and the steric hindrance imposed by the carbodiimides and the PEG reagents such as in branched chain molecules. It is therefore the preferred mode of PEG modification for Infergen and similar such proteins, native or expressed in a host system, which may have blocked N-termini to varying degrees to improve efficiencies and maintain higher in vivo biological activity.

Another method of achieving C-terminal PEGylation is as follows. Selectivity of C-terminal PEGylation is achieved with a sterically hindered reagent which excludes reactions at carboxyl residues either buried in the helices or internally in IFN-α. For example, one such reagent could be a branched chain PEG ~40 kd in molecular weight and this agent could be synthesized as follows:

OH$_3$C—(CH$_2$CH$_2$O)n-CH$_2$CH$_2$NH$_2$+Glutamic Acid i.e., HOCO—CH$_2$CH$_2$CH(NH2)-COOH is condensed with a suitable agent e.g., dicyclohexyl carbodiimide or water-soluble EDAC to provide the branched chain PEG agent OH$_3$C—(CH$_2$CH$_2$O)$_n$—CH$_2$CH$_2$NHCOCH(NH$_2$) CH$_2$OCH$_3$—(CH$_2$CH$_2$O)$_n$—CH$_2$CH$_2$NHCOCH$_2$.

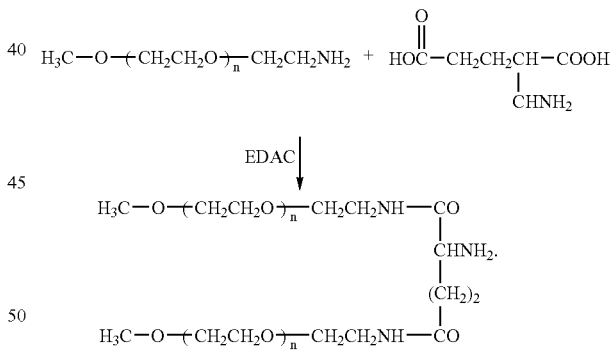

This reagent can be used in excess to couple the amino group with the free and flexible carboxyl group of IFN-α to form the peptide bond.

If desired, PEGylated IFN-α is separated from unPEGylated IFN-α using any known method, including, but not limited to, ion exchange chromatography, size exclusion chromatography, and combinations thereof. For example, where the PEG-IFN-α conjugate is a monoPEGylated IFN-α, the products are first separated by ion exchange chromatography to obtain material having a charge characteristic of monoPEGylated material (other multi-PEGylated material having the same apparent charge may be present), and then the monoPEGylated materials are separated using size exclusion chromatography.

IFN-β

The term interferon-beta ("IFN-β") includes IFN-β polypeptides that are naturally occurring; non-naturally-occurring IFN-β polypeptides; and analogs of naturally occurring or non-naturally occurring IFN-β that retain antiviral activity of a parent naturally-occurring or non-naturally occurring IFN-β.

Any of a variety of beta interferons can be administered in a subject method. Suitable beta interferons include, but are not limited to, naturally-occurring IFN-β; IFN-β1a, e.g., Avonex® (Biogen, Inc.), and Rebif® (Serono, SA); IFN-β1b (Betaseron®; Berlex); and the like.

The IFN-β formulation may comprise an N-blocked species, wherein the N-terminal amino acid is acylated with an acyl group, such as a formyl group, an acetyl group, a malonyl group, and the like. Also suitable for use is a consensus IFN-β.

IFN-β polypeptides can be produced by any known method. DNA sequences encoding IFN-β may be synthesized using standard methods. In many embodiments, IFN-β polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-β is "recombinant IFN-β." Where the host cell is a bacterial host cell, the IFN-β is modified to comprise an N-terminal methionine.

It is to be understood that IFN-β as described herein may comprise one or more modified amino acid residues, e.g., glycosylations, chemical modifications, and the like.

IFN-Tau

The term interferon-tau includes IFN-tau polypeptides that are naturally occurring; non-naturally-occurring IFN-tau polypeptides; and analogs of naturally occurring or non-naturally occurring IFN-tau that retain antiviral activity of a parent naturally-occurring or non-naturally occurring IFN-tau.

Suitable tau interferons include, but are not limited to, naturally-occurring IFN-tau; Tauferon® (Pepgen Corp.); and the like.

IFN-tau may comprise an amino acid sequence as set forth in any one of GenBank Accession Nos. P15696; P56828; P56832; P56829; P56831; Q29429; Q28595; Q28594; S08072; Q08071; Q08070; Q08053; P56830; P28169; P28172; and P28171. The sequence of any known IFN-tau polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-tau formulation may comprise an N-blocked species, wherein the N-terminal amino acid is acylated with an acyl group, such as a formyl group, an acetyl group, a malonyl group, and the like. Also suitable for use is a consensus IFN-tau.

IFN-tau polypeptides can be produced by any known method. DNA sequences encoding IFN-tau may be synthesized using standard methods. In many embodiments, IFN-tau polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-tau is "recombinant IFN-tau." Where the host cell is a bacterial host cell, the IFN-tau is modified to comprise an N-terminal methionine.

It is to be understood that IFN-tau as described herein may comprise one or more modified amino acid residues, e.g., glycosylations, chemical modifications, and the like.

IFN-ω

The term interferon-omega ("IFN-ω") includes IFN-ω polypeptides that are naturally occurring; non-naturally-occurring IFN-ω polypeptides; and analogs of naturally occurring or non-naturally occurring IFN-ω that retain antiviral activity of a parent naturally-occurring or non-naturally occurring IFN-ω.

Any known omega interferon can be administered in a subject method. Suitable IFN-ω include, but are not limited to, naturally-occurring IFN-ω; recombinant IFN-ω, e.g., Biomed 510 (BioMedicines); and the like.

IFN-ω may comprise an amino acid sequence as set forth in GenBank Accession No. NP_002168; or AAA70091. The sequence of any known IFN-ω polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-ω formulation may comprise an N-blocked species, wherein the N-terminal amino acid is acylated with an acyl group, such as a formyl group, an acetyl group, a malonyl group, and the like. Also suitable for use is a consensus IFN-ω.

IFN-ω polypeptides can be produced by any known method. DNA sequences encoding IFN-ω may be synthesized using standard methods. In many embodiments, IFN-ω polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-ω is "recombinant IFN-ω." Where the host cell is a bacterial host cell, the IFN-ω is modified to comprise an N-terminal methionine.

It is to be understood that IFN-ω as described herein may comprise one or more modified amino acid residues, e.g., glycosylations, chemical modifications, and the like.

Type II Interferon Receptor Agonists

Type II interferon receptor agonists include any naturally occurring or non-naturally-occurring ligand of a human Type II interferon receptor that binds to and causes signal transduction via the receptor. Type II interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

A specific example of a Type II interferon receptor agonist is IFN-gamma and variants thereof. While the present invention exemplifies use of an IFN-gamma polypeptide, it will be readily apparent that any Type II interferon receptor agonist can be used in a subject method.

Interferon-Gamma

The nucleic acid sequences encoding IFN-gamma polypeptides may be accessed from public databases, e.g., Genbank, journal publications, and the like. While various mammalian IFN-gamma polypeptides are of interest, for the treatment of human disease, generally the human protein will be used. Human IFN-gamma coding sequence may be found in Genbank, accession numbers X13274; V00543; and NM_000619. The corresponding genomic sequence may be found in Genbank, accession numbers J00219; M37265; and V00536. See, for example. Gray et al. (1982) *Nature* 295:501 (Genbank X13274); and Rinderknecht et al. (1984) *J.B.C.* 259:6790.

IFN-γ1b (Actimmune®; human interferon) is a single-chain polypeptide of 140 amino acids. It is made recombinantly in *E. coli* and is unglycosylated (Rinderknecht et al. 1984, *J. Biol. Chem.* 259:6790-6797). Recombinant IFN-gamma as discussed in U.S. Pat. No. 6,497,871 is also suitable for use herein.

The IFN-gamma to be used in the methods of the present invention may be any of natural IFN-gamma, recombinant IFN-gamma and the derivatives thereof so far as they have an IFN-γ activity, particularly human IFN-gamma activity. Human IFN-gamma exhibits the antiviral and anti-proliferative properties characteristic of the interferons, as well as a number of other immunomodulatory activities, as is known in the art. Although IFN-gamma is based on the sequences as provided above, the production of the protein and proteolytic processing can result in processing variants thereof. The unprocessed sequence provided by Gray et al., supra, consists of 166 amino acids (aa). Although the recombinant IFN-gamma produced in *E. coli* was originally believed to be 146 amino acids, (commencing at amino acid 20) it was subsequently found that native human IFN-gamma is cleaved after residue 23, to produce a 143 aa protein, or 144 aa if the terminal methionine is present, as required for expression in bacteria. During purification, the mature protein can additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG that, in the particular case of *E. coli* expression is not processed away. In other microbial systems or eukaryotic expression systems, methionine may be removed.

For use in the subject methods, any of the native IFN-gamma peptides, modifications and variants thereof, or a combination of one or more peptides may be used. IFN-gamma peptides of interest include fragments, and can be variously truncated at the carboxyl terminus relative to the full sequence. Such fragments continue to exhibit the characteristic properties of human gamma interferon, so long as amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925. Native IFN-gamma moieties include molecules variously extending from amino acid residues 24-150; 24-151, 24-152; 24-153, 24-155; and 24-157. Any of these variants, and other variants known in the art and having IFN-γ activity, may be used in the present methods.

The sequence of the IFN-γ polypeptide may be altered in various ways known in the art to generate targeted changes in sequence. A variant polypeptide will usually be substantially similar to the sequences provided herein, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. IFN-gamma may be modified with one or more polyethylene glycol moieties (PEGylated). In one embodiment, the invention contemplates the use of IFN-gamma variants with one or more non-naturally occurring glycosylation and/or pegylation sites that are engineered to provide glycosyl- and/or PEG-derivatized polypeptides with reduced serum clearance, such as the IFN-gamma polypeptide variants described in International Patent Publication No. WO 01/36001. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

Included in the subject invention are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see, for example, Friedler et al. 2000, *J. Biol. Chem.* 275:23783-23789). Analogs may be used that include residues other than naturally occurring L-amino acids, e.g., D-amino acids or non-naturally occurring synthetic amino acids. The protein may be pegylated to enhance stability.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Pirfenidone and Analogs Thereof

Pirfenidone (5-methyl-1-phenyl-2-(1H)-pyridone) and specific pirfenidone analogs are disclosed for the treatment of proliferative conditions, and are also useful in a subject treatment method, for example in the treatment of fibrotic disease, cancer, disease mediated by angiogenesis, etc.

Pirfenidone

Pirfenidone analogs

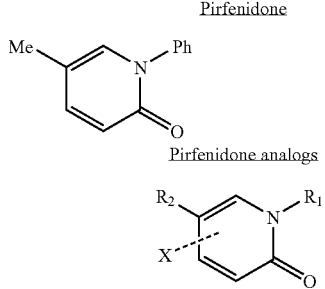

I.

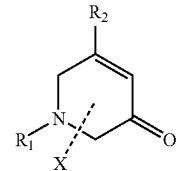

II.A

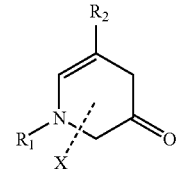

II.B

Descriptions for Substituents $R_1$, $R_2$, X $R_1$: carbocyclic (saturated and unsaturated), heterocyclic (saturated or unsaturated), alkyls (saturated and unsaturated). Examples include phenyl, benzyl, pyrimidyl, naphthyl, indolyl, pyrrolyl, furyl, thienyl, imidazolyl, cyclohexyl, piperidyl, pyrrolidyl, morpholinyl, cyclohexenyl, butadienyl, and the like.

$R_1$ can further include substitutions on the carbocyclic or heterocyclic moieties with substituents such as halogen, nitro, amino, hydroxyl, alkoxy, carboxyl, cyano, thio, alkyl, aryl, heteroalkyl, heteroaryl and combinations thereof, for example, 4-nitrophenyl, 3-chlorophenyl, 2,5-dinitrophenyl, 4-methoxyphenyl, 5-methyl-pyrrolyl, 2,5-dichlorocyclohexyl, guanidinyl-cyclohexenyl and the like.

$R_2$: alkyl, carbocyclic, aryl, heterocyclic. Examples include: methyl, ethyl, propyl, isopropyl, phenyl, 4-nitrophenyl, thienyl and the like.

X: may be any number (from 1 to 3) of substituents on the carbocyclic or heterocyclic ring. The substituents can be the same or different. Substituents can include hydrogen, alkyl, heteroalkyl, aryl, heteroaryl, halo, nitro, carboxyl, hydroxyl, cyano, amino, thio, alkylamino, haloaryl and the like.

The substituents may be optionally further substituted with 1-3 substituents from the group consisting of alkyl, aryl, nitro, alkoxy, hydroxyl and halo groups. Examples include: methyl, 2,3-dimethyl, phenyl, p-tolyl, 4-chlorophenyl, 4-nitrophenyl, 2,5-dichlorophenyl, furyl, thienyl and the like.

Specific Examples include those shown in Table 1:

TABLE 1

| IA | IIB |
|---|---|
| 5-Methyl-1-(2'-pyridyl)-2-(1H) pyridine, | 6-Methyl-1-phenyl-3-(1H) pyridone, |
| 6-Methyl-1-phenyl-2-(1H) pyridone, | 5-Methyl-1-p-tolyl-3-(1H) pyridone, |
| 5-Methyl-3-phenyl-1-(2'-thienyl)-2-(1H) pyridone, | 5-Methyl-1-(2'-naphthyl)-3-(1H) pyridone, |
| 5-Methyl-1-(2'-naphthyl)-2-(1H) pyridone, | 5-Methyl-1-phenyl-3-(1H) pyridone, |
| 5-Methyl-1-p-tolyl-2-(1H) pyridone, | 5-Methyl-1-(5'-quinolyl)-3-(1H) pyridone, |
| 5-Methyl-1-(1'naphthyl)-2-(1H) pyridone, | 5-Ethyl-1-phenyl-3-(1H) pyridone, |
| 5-Ethyl-1-phenyl-2-(1H) pyridone, | 5-Methyl-1-(4'-methoxyphenyl)-3-(1H) pyridone, |
| 5-Methyl-1-(5'-quinolyl)-2-(1H) pyridone, | 4-Methyl-1-phenyl-3-(1H) pyridone, |
| 5-Methyl-1-(4'-quinolyl)-2-(1H) pyridone, | 5-Methyl-1-(3'-pyridyl)-3-(1H) pyridone, |
| 5-Methyl-1-(4'-pyridyl)-2-(1H) pyridone, | 5-Methyl-1-(2'-Thienyl)-3-(1H) pyridone, |
| 3-Methyl-1-phenyl-2-(1H) pyridone, | 5-Methyl-1-(2'-pyridyl)-3-(1H) pyridone, |
| 5-Methyl-1-(4'-methoxyphenyl)-2-(1H) pyridone, | 5-Methyl-1-(2'-quinolyl)-3-(1H) pyridone, |
| 1-Phenyl-2-(1H) pyridone, | 1-Phenyl-3-(1H) pyridine, |
| 1,3-Diphenyl-2-(1H) pyridone, | 1-(2'-Furyl)-5-methyl-3-(1H) pyridone, |
| 1,3-Diphenyl-5-methyl-2-(1H) pyridone, | 1-(4'-Chlorophenyl)-5-methyl-3-(1H) pyridine. |
| 5-Methyl-1-(3'-trifluoromethylphenyl)-2-(1H)-pyridone, | |

TABLE 1-continued

| IA | IIB |
|---|---|
| 3-Ethyl-1-phenyl-2-(1H) pyridone, | |
| 5-Methyl-1-(3'-pyridyl)-2-(1H) pyridone, | |
| 5-Methyl-1-(3-nitrophenyl)-2-(1H) pyridone, | |
| 3-(4'-Chlorophenyl)-5-Methyl-1-phenyl-2-(1H) pyridone, | |
| 5-Methyl-1-(2'-Thienyl)-2-(1H) pyridone, | |
| 5-Methyl-1-(2'-thiazolyl)-2-(1H) pyridone, | |
| 3,6-Dimethyl-1-phenyl-2-(1H) pyridone, | |
| 1-(4'Chlorophenyl)-5-Methyl-2-(1H) pyridone, | |
| 1-(2'-Imidazolyl)-5-Methyl-2-(1H) pyridone, | |
| 1-(4'-Nitrophenyl)-2-(1H) pyridone, | |
| 1-(2'-Furyl)-5-Methyl-2-(1H) pyridone, | |
| 1-Phenyl-3-(4'-chlorophenyl)-2-(1H) pyridine. | |

U.S. Pat. Nos. 3,974,281; 3,839,346; 4,042,699; 4,052,509; 5,310,562; 5,518,729; 5,716,632; and 6,090,822 describe methods for the synthesis and formulation of pirfenidone and specific pirfenidone analogs in pharmaceutical compositions suitable for use in the methods of the present invention.

Type III Interferon Receptor Agonists

Type III interferon receptor agonists can be used in a subject treatment method. Type III interferon agonists include an IL-28b polypeptide; and IL-28a polypeptide; and IL-29 polypeptide; antibody specific for a Type III interferon receptor; and any other agonist of Type III interferon receptor, including non-polypeptide agonists.

IL-28A, IL-28B, and IL-29 (referred to herein collectively as "Type III interferons" or "Type III IFNs") are described in Sheppard et al. (2003) Nature 4:63-68. Each polypeptide binds a heterodimeric receptor consisting of IL-10 receptor β chain and an IL-28 receptor α. Sheppard et al. (2003), supra. The amino acid sequences of IL-28A, IL-28B, and IL-29 are found under GenBank Accession Nos. NP_742150, NP_742151, and NP_742152, respectively.

The amino acid sequence of a Type III IFN polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Included for use in the subject invention are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) J. Biol. Chem. 275:23783-23789). Analogs may be used that include residues other than naturally occurring L-amino acids, e.g. D-amino acids or non-naturally occurring synthetic amino acids. The protein may be pegylated to enhance stability. The polypeptides may be fused to albumin.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

TNF Antagonists

Suitable TNF-α antagonists for use herein include agents that decrease the level of TNF-α synthesis, agents that block or inhibit the binding of TNF-α to a TNF-α receptor (TNFR), and agents that block or inhibit TNFR-mediated signal transduction. Unless otherwise expressly stated, every reference to a "TNF-α antagonist" or "TNF antagonist" herein will be understood to mean a TNF-α antagonist other than pirfenidone or a pirfenidone analog.

As used herein, the terms "TNF receptor polypeptide" and "TNFR polypeptide" refer to polypeptides derived from TNFR (from any species) which are capable of binding TNF. Two distinct cell-surface TNFRs have described: Type II TNFR (or p75 TNFR or TNFRII) and Type I TNFR (or p55 TNFR or TNFRI). The mature full-length human p75 TNFR is a glycoprotein having a molecular weight of about 75-80 kilodaltons (kD). The mature full-length human p55 TNFR is a glycoprotein having a molecular weight of about 55-60 kD.

Exemplary TNFR polypeptides are derived from TNFR Type I and/or TNFR type II. Soluble TNFR includes p75 TNFR polypeptide; fusions of p75 TNFR with heterologous fusion partners, e.g., the Fc portion of an immunoglobulin.

TNFR polypeptide may be an intact TNFR or a suitable fragment of TNFR. U.S. Pat. No. 5,605,690 provides examples of TNFR polypeptides, including soluble TNFR polypeptides, appropriate for use in the present invention. In many embodiments, the TNFR polypeptide comprises an extracellular domain of TNFR. In some embodiments, the TNFR polypeptide is a fusion polypeptide comprising an extracellular domain of TNFR linked to a constant domain of an immunoglobulin molecule. In other embodiments, the TNFR polypeptide is a fusion polypeptide comprising an extracellular domain of the p75 TNFR linked to a constant domain of an IgG1 molecule. In some embodiments, when administration to humans is contemplated, an Ig used for fusion proteins is human, e.g., human IgG1.

Monovalent and multivalent forms of TNFR polypeptides may be used in the present invention. Multivalent forms of TNFR polypeptides possess more than one TNF binding site. In some embodiments, the TNFR is a bivalent, or dimeric, form of TNFR. For example, as described in U.S. Pat. No. 5,605,690 and in Mohler et al., 1993, J. Immunol., 151:1548-1561, a chimeric antibody polypeptide with TNFR extracellular domains substituted for the variable domains of either or both of the immunoglobulin heavy or light chains would provide a TNFR polypeptide for the present invention. Generally, when such a chimeric TNFR: antibody polypeptide is produced by cells, it forms a bivalent molecule through disulfide linkages between the immunoglobulin domains. Such a chimeric TNFR:antibody polypeptide is referred to as TNFR:Fc.

In one embodiment, a subject method involves administration of an effective amount of the soluble TNFR ENBREL® etanercept. ENBREL® is a dimeric fusion protein consisting of the extracellular ligand-binding portion of the human 75 kilodalton (p75) TNFR linked to the Fc portion of human IgG1. The Fc component of ENBREL® contains the CH2 domain, the CH3 domain and hinge region, but not the CH1 domain of IgG1. ENBREL® is produced in a Chinese hamster ovary (CHO) mammalian cell expression system. It consists of 934 amino acids and has an apparent molecular weight of approximately 150 kilodaltons. Smith et al. (1990) *Science* 248:1019-1023; Mohler et al. (1993) *J. Immunol.* 151:1548-1561; U.S. Pat. No. 5,395,760; and U.S. Pat. No. 5,605,690.

Also suitable for use are monoclonal antibodies that bind TNF-α. Monoclonal antibodies include "humanized" mouse monoclonal antibodies; chimeric antibodies; monoclonal antibodies that are at least about 80%, at least about 90%, at least about 95%, or 100% human in amino acid sequence; and the like. See, e.g., WO 90/10077; WO 90/04036; and WO 92/02190. Suitable monoclonal antibodies include antibody fragments, such as Fv, F(ab')$_2$ and Fab; synthetic antibodies; artificial antibodies; phage display antibodies; and the like.

Examples of suitable monoclonal antibodies include infliximab (REMICADE®, Centocor); and adalimumab (HUMIRA™, Abbott) REMICADE® is a chimeric monoclonal anti-TNF-α antibody that includes about 25% mouse amino acid sequence and about 75% human amino acid sequence. REMICADE® comprises a variable region of a mouse monoclonal anti-TNF-α antibody fused to the constant region of a human IgG1. Elliott et al. (1993) *Arthritis Rheum.* 36:1681-1690; Elliott et al. (1994) *Lancet* 344:1105-1110; Baert et al. (1999) *Gastroenterology* 116:22-28. HUMIRA™ is a human, full-length IgG1 monoclonal antibody that was identified using phage display technology. Piascik (2003) *J. Am. Pharm. Assoc.* 43:327-328.

Also included in the term "TNF antagonist," and therefore suitable for use in a subject method, are stress-activated protein kinase (SAPK) inhibitors. SAPK inhibitors are known in the art, and include, but are not limited to 2-alkyl imidazoles disclosed in U.S. Pat. No. 6,548,520; 1,4,5-substituted imidazole compounds disclosed in U.S. Pat. No. 6,489,325; 1,4, 5-substituted imidazole compounds disclosed in U.S. Pat. No. 6,569,871; heteroaryl aminophenyl ketone compounds disclosed in Published U.S. patent application No. 2003/0073832; pyridyl imidazole compounds disclosed in U.S. Pat. No. 6,288,089; and heteroaryl aminobenzophenones disclosed in U.S. Pat. No. 6,432,962. Also of interest are compounds disclosed in U.S. patent application Publication No. 2003/0149041; and U.S. Pat. No. 6,214,854. A stress-activated protein kinase is a member of a family of mitogen-activated protein kinases which are activated in response to stress stimuli. SAPK include, but are not limited to, p38 (Lee et al. (1994) *Nature* 372:739) and c-jun N-terminal kinase (JNK).

Methods to assess TNF antagonist activity are known in the art and exemplified herein. For example, TNF antagonist activity may be assessed with a cell-based competitive binding assay. In such an assay, radiolabeled TNF is mixed with serially diluted TNF antagonist and cells expressing cell membrane bound TNFR. Portions of the suspension are centrifuged to separate free and bound TNF and the amount of radioactivity in the free and bound fractions determined. TNF antagonist activity is assessed by inhibition of TNF binding to the cells in the presence of the TNF antagonist.

As another example, TNF antagonists may be analyzed for the ability to neutralize TNF activity in vitro in a bioassay using cells susceptible to the cytotoxic activity of TNF as target cells. In such an assay, target cells, cultured with TNF, are treated with varying amounts of TNF antagonist and subsequently are examined for cytolysis. TNF antagonist activity is assessed by a decrease in TNF-induced target cell cytolysis in the presence of the TNF antagonist.

Dosages, Formulations, and Routes of Administration

A therapeutic agent (e.g., pirfenidone or a pirfenidone analog; and optionally one or more additional therapeutic agents) that is administered to an individual in a subject method is administered to individuals in a formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. The terms "therapeutic agent" and "active agent" are used interchangeably herein.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, the active agents may be administered to the host using any convenient means capable of resulting in the desired therapeutic effect. Thus, the agents can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of an active agent (e.g., pirfenidone, a pirfenidone analog, a Type I interferon receptor agonist, a Type II interferon receptor agonist, a non-pirfenidone TNF-α antagonist, an anti-fibrotic agent, etc.) can be achieved in various ways, including oral, buccal, rectal, parenteral, intraperitoneal, intradermal, subcutaneous, intramuscular, transdermal, intratracheal, etc., administration. In some embodiments, two different routes of administration are used.

Subcutaneous administration of a therapeutic agent can be accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of an agent to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system.

In some embodiments, a therapeutic agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present treatment methods can be accomplished using any of a variety of refillable, pump systems. Pumps provide consistent, controlled release over time. Typically, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are generally preferred in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, the present treatment methods can be accomplished using any of a variety of refillable, non-exchangeable pump systems. Pumps and other convective systems are preferred in some embodiments due to their generally more consistent, controlled release over time. Osmotic pumps are particularly preferred due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, a therapeutic agent is delivered using an implantable drug delivery system, e.g., a system that is programmable to provide for administration of a therapeutic agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

In pharmaceutical dosage forms, an active agent may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for an active agent depend on the particular active agent employed and the effect to be achieved, and the pharmacodynamics associated with each active agent in the host.

In connection with each of the methods described herein, the invention provides embodiments in which the therapeutic agent(s) is/are administered to the patient by a controlled drug delivery device. In some embodiments, a therapeutic agent is delivered to the patient substantially continuously or continuously by the controlled drug delivery device. Optionally, an implantable infusion pump is used to deliver a therapeutic agent to the patient substantially continuously or continuously by subcutaneous infusion.

In other embodiments, a therapeutic agent is administered to the patient so as to achieve and maintain a desired average daily serum concentration of the therapeutic agent at a substantially steady state for the duration of the therapy. Optionally, an implantable infusion pump is used to deliver the therapeutic agent to the patient by subcutaneous infusion so as to achieve and maintain a desired average daily serum concentration of the therapeutic agent at a substantially steady state for the duration of the therapy.

Effective dosages of pirfenidone or a specific pirfenidone analog include a weight-based dosage in the range from about 5 mg/kg/day to about 125 mg/kg/day, or a fixed dosage of about 400 mg to about 3600 mg per day, or about 800 mg to about 2400 mg per day, or about 1000 mg to about 1800 mg per day, or about 1200 mg to about 1600 mg per day, administered orally. Other doses and formulations of pirfenidone and specific pirfenidone analogs suitable are described in U.S. Pat. Nos. 5,310,562; 5,518,729; 5,716,632; and 6,090,822.

In many embodiments, a pirfenidone or pirfenidone analog is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The pirfenidone or pirfenidone analog can be administered tid, bid, qd, qod, biw, tiw, qw, qow, three times per month, once monthly, substantially continuously, or continuously.

In many embodiments, multiple doses of a pirfenidone or pirfenidone analog are administered. For example, a pirfenidone or pirfenidone analog is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Those of skill in the art will readily appreciate that dose levels can vary as a function of the specific compounds (active agents), the severity of the symptoms and the susceptibility of the subject to side effects. Preferred dosages for a given compound are readily determinable by those of skill in the art by a variety of means. A preferred means is to measure the physiological potency of a given compound.

In some embodiments, a pirfenidone or pirfenidone analog is administered in combination therapy with at least a second therapeutic agent. In some of these embodiments, a second therapeutic agent is administered throughout the entire course of pirfenidone/pirfenidone analog treatment. In other embodiments, a second therapeutic agent is administered less than the entire course of pirfenidone/pirfenidone analog treatment, e.g., only during the first phase of pirfenidone/pirfenidone analog treatment, only during the second phase of pirfenidone/pirfenidone analog treatment, or some other portion of the pirfenidone/pirfenidone analog treatment regimen.

In some embodiments, a subject combination therapy involves co-administering pirfenidone or a pirfenidone analog and a Type II interferon receptor agonist. In some of these embodiments, the Type II interferon receptor agonist is an IFN-γ.

Effective dosages of IFN-γ can range from about 0.5 μg/m$^2$ to about 500 μg/m$^2$, usually from about 1.5 μg/m$^2$ to 200 μg/m$^2$, depending on the size of the patient. This activity is based on $10^6$ international units (U) per 50 μg of protein. IFN-γ can be administered daily, every other day, three times a week, or substantially continuously or continuously.

In specific embodiments of interest, IFN-γ is administered to an individual in a unit dosage form of from about 25 μg to about 500 μg, from about 50 μg to about 400 μg, or from about 100 μg to about 300 μg. In particular embodiments of interest, the dose is about 200 μg IFN-γ. In many embodiments of interest, IFN-γ1b is administered.

Where the dosage is 200 μg IFN-γ per dose, the amount of IFN-γ per body weight (assuming a range of body weights of from about 45 kg to about 135 kg) is in the range of from about 4.4 μg IFN-γ per kg body weight to about 1.48 μg IFN-γ per kg body weight.

The body surface area of subject individuals generally ranges from about 1.33 m$^2$ to about 2.50 m$^2$. Thus, in many embodiments, an IFN-γ dosage ranges from about 150 μg/m$^2$ to about 20 μg/m$^2$. For example, an IFN-1 dosage ranges from about 20 μg/m$^2$ to about 30 μg/m$^2$, from about 30 μg/m$^2$ to about 40 μg/m$^2$, from about 40 μg/m$^2$ to about 50 μg/m$^2$, from about 50 μg/m$^2$ to about 60 μg/m$^2$, from about 60 μg/m$^2$ to about 70 μg/m$^2$, from about 70 μg/m$^2$ to about 80 μg/m$^2$, from about 80 μg/m² to about 90 μg/m², from about 90 μg/m² to about 100 μg/m², from about 100 μg/m² to about 110 μg/m², from about 110 μg/m² to about 120 μg/m², from about 120 μg/m² to about 130 μg/m², from about 130 μg/m² to about 140 μg/m², or from about 140 μg/m² to about 150 μg/m². In some embodiments, the dosage groups range from about 25 μg/m² to about 100 μg/m². In other embodiments, the dosage groups range from about 25 μl/m² to about 50 μg/m².

In many embodiments, IFN-γ is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. IFN-γ can be administered tid, bid, qd, qod, biw, tiw, qw, qow, three times per month, once monthly, substantially continuously, or continuously.

In many embodiments, multiple doses of IFN-γ are administered. For example, IFN-γ is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In other embodiments, a subject combination therapy involves co-administering pirfenidone or a pirfenidone analog and a Type I interferon receptor agonist. In some embodiments, the Type I interferon receptor agonist is an IFN-α. Effective dosages of an IFN-α range from about 3 μg to about 27 μg, from about 3 MU to about 10 MU, from about 90 μg to about 180 μg, or from about 18 μg to about 90 μg.

Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS®PEGylated IFN-α2a contain an amount of about 90 μg to 270 μg, or about 180 μg, of drug per dose. Effective dosages of PEG-INTRON® PEGylated IFN-α2b contain an amount of about 0.5 μg to 3.0 μg of drug per kg of body weight per dose. Effective dosages of PEGylated consensus interferon (PEG-CIFN) contain an amount of about 18 μg to about 90 μg, or from about 27 μg to about 60 μg, or about 45 μg, of CIFN amino acid weight per dose of PEG-CIFN. Effective dosages of monoPEG (30 kD, linear)-ylated CIFN contain an amount of about 45 μg to about 270 μg, or about 60 μg to about 180 μg, or about 90 μg to about 120 μg, of drug per dose. IFN-α can be administered daily, every other day, once a week, three times a week, every other week, three times per month, once monthly, substantially continuously or continuously.

In other embodiments, a subject combination therapy involves co-administering pirfenidone or a pirfenidone analog and a TNF antagonist. Effective dosages of a TNF-α antagonist range from 0.1 μg to 40 mg per dose, e.g., from about 0.1 μg to about 0.5 μg per dose, from about 0.5 μg to about 1.0 μg per dose, from about 1.0 μg per dose to about 5.0 μg per dose, from about 5.0 μg to about 10 μg per dose, from about 10 μg to about 20 μg per dose, from about 20 μg per dose to about 30 μg per dose, from about 30 μg per dose to about 40 μg per dose, from about 40 μg per dose to about 50 μg per dose, from about 50 μg per dose to about 60 μg per dose, from about 60 μg per dose to about 70 μg per dose, from about 70 μg to about 80 μg per dose, from about 80 μg per dose to about 100 μg per dose, from about 100 μg to about 150 μg per dose, from about 150 μg to about 200 μg per dose, from about 200 μg per dose to about 250 μg per dose, from about 250 μg to about 300 μg per dose, from about 300 μg to about 400 μg per dose, from about 400 μg to about 500 μg per dose, from about 500 μg to about 600 μg per dose, from about 600 μg to about 700 μg per dose, from about 700 μg to about 800 μg per dose, from about 800 μg to about 900 μg per dose, from about 900 μg to about 1000 μg per dose, from about 1 mg to about 10 mg per dose, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, the TNF-α antagonist is ENBREL® etanercept. Effective dosages of etanercept range from about 0.1 μg to about 40 mg per dose, from about 0.1 μg to about 1 μg per dose, from about 1 μg to about 10 μg per dose, from about 10 μg to about 100 μg per dose, from about 100 μg to about 1 mg per dose, from about 1 mg to about 5 mg per dose, from about 5 mg to about 10 mg, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, effective dosages of a TNF-α antagonist are expressed as mg/kg body weight. In these embodiments, effective dosages of a TNF-α antagonist are from about 0.1 mg/kg body weight to about 10 mg/kg body weight, e.g., from about 0.1 mg/kg body weight to about 0.5 mg/kg body weight, from about 0.5 mg/kg body weight to about 1.0 mg/kg body weight, from about 1.0 mg/kg body weight to about 2.5 mg/kg body weight, from about 2.5 mg/kg body weight to about 5.0 mg/kg body weight, from about 5.0 mg/kg body weight to about 7.5 mg/kg body weight, or from about 7.5 mg/kg body weight to about 10 mg/kg body weight.

In some embodiments, the TNF-α antagonist is REMICADE®. Effective dosages of REMICADE® range from about 0.1 mg/kg to about 10 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, from about 4.0 mg/kg to about 4.5 mg/kg, from about 4.5 mg/kg to about 5.0 mg/kg, from about 5.0 mg/kg to about 7.5 mg/kg, or from about 7.5 mg/kg to about 10 mg/kg per dose.

In some embodiments the TNF-α antagonist is HUMIRA™. Effective dosages of HUMIRA™ range from about 0.1 μg to about 35 mg, from about 0.1 μg to about 1 μg, from about 1 μg to about 10 μg, from about 10 μg to about 100 μg, from about 100 μg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, or from about 35 mg to about 40 mg per dose.

In many embodiments, a TNF-α antagonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The TNF-α antagonist can be administered tid, bid, qd, qod, biw, tiw, qw, qow, three times per month, once monthly, once bimonthly, substantially continuously, or continuously.

In many embodiments, multiple doses of a TNF-α antagonist are administered. For example, a TNF-α antagonist is administered once bimonthly, once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Those of skill in the art will readily appreciate that dose levels can vary as a function of the specific compounds, the severity of the symptoms and the susceptibility of the subject to side effects. Preferred dosages for a given compound are readily determinable by those of skill in the art by a variety of means. A preferred means is to measure the physiological potency of a given compound.

Side Effect Management Agents

In some embodiments, a subject combination therapy further includes administering a side effect management agent that reduces a side effect of a therapeutic agent, in an amount effective to reduce at least one side effect. Side effect management agents include palliative agents, and other agents for the treatment, reduction, or avoidance of a side effect caused by any therapeutic agent.

In some embodiments, a subject combination therapy further includes administering a side effect management palliative agent that reduces a side effect of a pirfenidone or pirfenidone analog in an amount effective to reduce at least one side effect. Side effects of pirfenidone or pirfenidone analog treatment include gastrointestinal disturbances and discomfort. Gastrointestinal disturbances include nausea, diarrhea, gastrointestinal cramping, and the like. In some embodiments, an effective amount of a side effect management palliative agent reduces a side effect induced by treatment with a pirfenidone or pirfenidone analog by at least about 10%, at least about 20%, at least about 30%, at least about 40%, at least about 50%, at least about 60%, or more, compared to the rate of occurrence or the degree or extent of the side effect when the pirfenidone or pirfenidone analog therapy is administered without the palliative side effect management agent.

Side effects of Type II interferon receptor agonist treatment include, but are not limited to, fever, malaise, tachycardia, chills, headache, arthralgia, myalgia, myelosuppression, suicide ideation, platelet suppression, neutropenia, lymphocytopenia, erythrocytopenia (anemia), and anorexia. In some embodiments, an effective amount of a side effect management agent reduces a side effect induced by treatment with a Type II interferon receptor agonist by at least about 10%, at least about 20%, at least about 30%, at least about 40%, at least about 50%, at least about 60%, or more, compared to the rate of occurrence or the degree or extent of the side effect when the Type II interferon receptor agonist therapy is administered without the side effect management agent. For example, if a fever is experienced with the Type II interferon receptor agonist therapy, then the body temperature of an individual treated with the Type II interferon receptor agonist therapy and side effect management agent according to the instant invention is reduced by at least 0.5 degree Fahrenheit, and in some embodiments is within the normal range, e.g., at or near 98.6° F.

Suitable side effect management agents include agents that are effective in pain management; agents that ameliorate gastrointestinal discomfort; analgesics, anti-inflammatories, antipsychotics, antineurotics, anxiolytics, hematopoietic agents, and agents that reduce gastrointestinal discomfort. In addition, the invention contemplates the use of any compound for palliative care of patients suffering from pain or any other side effect in the course of treatment with a subject monotherapy or combination therapy. Exemplary side effect management agents include acetaminophen, ibuprofen, and other NSAIDs, H2 blockers, hematopoietic agents, and antacids.

Suitable H2 blockers (histamine type 2 receptor antagonists) that are suitable for use as a side effect management agent in a subject therapy include, but are not limited to, Cimetidine (e.g., Tagamet, Peptol, Nu-cimet, apo-cimetidine, non-cimetidine); Ranitidine (e.g., Zantac, Nu-ranit, Novorandine, and apo-ranitidine); and Famotidine (Pepcid, Apo-Famotidine, and Novo-Famotidine).

Suitable antacids include, but are not limited to, aluminum and magnesium hydroxide (Maalox®, Mylanta®); aluminum carbonate gel (Basajel®); aluminum hydroxide (Amphojel®, AlternaGEL®); calcium carbonate (Tums®, Titralac®); magnesium hydroxide; and sodium bicarbonate.

Suitable non-steroidal anti-inflammatory drugs (NSAIDs) include, but are not limited to, acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing.

Suitable hematopoietic agents include agents that prevent or restore depressed blood cell populations, including, but not limited to, erythropoietins, such as EPOGEN™ epoetin-alfa, granulocyte colony stimulating factors (G-CSFs), such as NEUPOGEN™ filgrastim, granulocyte-macrophage colony stimulating factors (GM-CSFs), thrombopoietins, etc.

Additional Therapeutic Agents

In some embodiments, a subject monotherapy or combination therapy is augmented with an additional therapeutic agent. Suitable additional therapeutic agents include, but are not limited to, anti-cancer agents (e.g., anti-neoplastic agents, anti-proliferative agents, cytotoxic agents), anti-angiogenic agents, and anti-fibrotic agents.

Anti-Proliferative Agents and Therapies

In some embodiments, a subject monotherapy or combination therapy is administered as adjuvant therapy to a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indoledziones, e.g. mitomycin; macrocyclic immunosuppressants, e.g. cyclosporine, FK-506 (tacrolirnus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; (9) inhibitors of angiogenesis; and (10) antagonists of tumor necrosis factor.

In one aspect, the invention contemplates a subject monotherapy or combination therapy as an adjuvant to any therapy in which the cancer patient receives treatment with least one additional antineoplastic drug, where the additional drug is a tyrosine kinase inhibitor. In some embodiments, the tyrosine kinase inhibitor is a receptor tyrosine kinase (RTK) inhibitor, such as type I receptor tyrosine kinase inhibitors (e.g., inhibitors of epidermal growth factor receptors), type II receptor tyrosine kinase inhibitors (e.g., inhibitors of insulin receptor), type III receptor tyrosine kinase inhibitors (e.g., inhibitors of platelet-derived growth factor receptor), and type IV receptor tyrosine kinase inhibitors (e.g., fibroblast growth factor receptor). In other embodiments, the tyrosine kinase inhibitor is a non-receptor tyrosine kinase inhibitor, such as inhibitors of src kinases or janus kinases.

In another aspect, the invention contemplates a subject monotherapy or combination therapy as an adjuvant to any therapy in which the cancer patient receives treatment with least one additional antineoplastic drug, where the additional drug is an inhibitor of a receptor tyrosine kinase involved in growth factor signaling pathway(s). In some embodiments, the inhibitor is genistein. In other embodiments, the inhibitor is an EGFR tyrosine kinase-specific antagonist, such as IRESSA™ gefitinib (ZD18398; Novartis), TARCEVA™ erolotinib (OSI-774; Roche; Genentech; OSI Pharmaceuticals), or tyrphostin AG1478 (4-(3-chloroanilino)-6,7-dimethoxyquinazoline. In still other embodiments, the inhibitor is any indolinone antagonist of Flk-1/KDR (VEGF-R2) tyrosine kinase activity described in U.S. patent application Publication No. 2002/0183 364 A1, such as the indolinone antagonists of Flk-1/KDR (VEGF-R2) tyrosine kinase activity disclosed in Table 1 on pages 4-5 thereof. In further embodiments, the inhibitor is any of the substituted 3-[(4,5,6,7-tetrahydro-1H-indol-2-yl)methylene]-1,3-dihydroindol-2-one antagonists of Flk-1/KDR (VEGF-R2), FGF-R1 or PDGF-R tyrosine kinase activity disclosed in Sun, L., et al., *J. Med. Chem.*, 43(14): 2655-2663 (2000). In additional embodiments, the inhibitor is any substituted 3-[(3- or 4-carboxyethylpyrrol-2-yl) methylidenyl]indolin-2-one antagonist of Flt-1 (VEGF-R1), Flk-1/KDR (VEGF-R2), FGF-R1 or PDGF-R tyrosine kinase activity disclosed in Sun, L., et al., *J. Med. Chem.*, 42(25): 5120-5130 (1999).

In another aspect, the invention contemplates a subject monotherapy or combination therapy as an adjuvant to any therapy in which the cancer patient receives treatment with least one additional antineoplastic drug, where the additional drug is an inhibitor of a non-receptor tyrosine kinase involved in growth factor signaling pathway(s). In some embodiments, the inhibitor is an antagonist of JAK2 tyrosine kinase activity, such as tyrphostin AG490 (2-cyano-3-(3,4-dihydroxyphenyl)-N-(benzyl)-2-propenamide). In other embodiments, the inhibitor is an antagonist of bcr-abl tyrosine kinase activity, such as GLEEVEC™ imatinib mesylate (STI-571; Novartis).

In another aspect, the invention contemplates a subject monotherapy or combination therapy as an adjuvant to any therapy in which the cancer patient receives treatment with least one additional antineoplastic drug, where the additional drug is a serine/threonine kinase inhibitor. In some embodiments, the serine/threonine kinase inhibitor is a receptor serine/threonine kinase inhibitor, such as antagonists of TGF-β receptor serine/threonine kinase activity. In other embodiments, the serine/threonine kinase inhibitor is a non-receptor serine/threonine kinase inhibitor, such as antagonists of the serine/threonine kinase activity of the MAP kinases, protein kinase C (PKC), protein kinase A (PKA), or the cyclin-dependent kinases (CDKs).

In another aspect, the invention contemplates a subject monotherapy or combination therapy as an adjuvant to any therapy in which the cancer patient receives treatment with least one additional antineoplastic drug, where the additional drug is an inhibitor of one or more kinases involved in cell cycle regulation. In some embodiments, the inhibitor is an antagonist of CDK2 activation, such as tryphostin AG490 (2-cyano-3-(3,4-dihydroxyphenyl)-N-(benzyl)-2-propenamide). In other embodiments, the inhibitor is an antagonist of CDK1/cyclin B activity, such as alsterpaullone. In still other embodiments, the inhibitor is an antagonist of CDK2 kinase activity, such as indirubin-3'-monoxime. In additional embodiments, the inhibitor is an ATP pool antagonist, such as lometrexol (described in U.S. patent application Publication No. 2002/0156023 A1).

In another aspect, the invention contemplates a subject monotherapy or combination therapy as an adjuvant to any therapy in which the cancer patient receives treatment with least one additional antineoplastic drug, where the additional drug is an a tumor-associated antigen antagonist, such as an antibody antagonist. In some embodiments involving the treatment of HER2-expressing tumors, the tumor-associated antigen antagonist is an anti-HER2 monoclonal antibody, such as HERCEPTIN™ trastuzumab. In some embodiments involving the treatment of CD20-expressing tumors, such as B-cell lymphomas, the tumor-associated antigen antagonist is an anti-CD20 monoclonal antibody, such as RITUXAN™ rituximab.

In another aspect, the invention contemplates a subject monotherapy or combination therapy as an adjuvant to any therapy in which the cancer patient receives treatment with least one additional antineoplastic drug, where the additional drug is a tumor growth factor antagonist. In some embodiments, the tumor growth factor antagonist is an antagonist of epidermal growth factor (EGF), such as an anti-EGF monoclonal antibody. In other embodiments, the tumor growth factor antagonist is an antagonist of epidermal growth factor receptor erbB1 (EGFR), such as an anti-EGFR monoclonal antibody inhibitor of EGFR activation or signal transduction.

In another aspect, the invention contemplates a subject monotherapy or combination therapy as an adjuvant to any therapy in which the cancer patient receives treatment with least one additional antineoplastic drug, where the additional drug is an Apo-2 ligand agonist. In some embodiments, the Apo-2 ligand agonist is any of the Apo-2 ligand polypeptides described in WO 97/25428.

Anti-Angiogenic Agents

Suitable anti-angiogenic agents include, but are not limited to, a vascular endothelial cell growth factor (VEGF) antagonist, such as an anti-VEGF monoclonal antibody, e.g. AVASTIN™ bevacizumab; a retinoic acid receptor (RXR) ligand; and a peroxisome proliferator-activated receptor (PPAR) gamma ligand.

In some embodiments, the invention contemplates a subject monotherapy or combination therapy, further comprising administering at least one additional drug, where the additional drug is an anti-angiogenic agent. In some embodiments, the anti-angiogenic agent is a vascular endothelial cell grown factor (VEGF) antagonist, such as an anti-VEGF monoclonal antibody, e.g. AVASTIN™ bevacizumab (Genentech). In other embodiments, the anti-angiogenic agent is a retinoic acid receptor (RXR) ligand, such as any RXR ligand described in U.S. patent application Publication No. 2001/0036955 A1 or in any of U.S. Pat. Nos. 5,824,685; 5,780,676; 5,399,586; 5,466,861; 4,810,804; 5,770,378; 5,770,383; or 5,770,382. In still other embodiments, the anti-angiogenic agent is a peroxisome proliferator-activated receptor (PPAR) gamma ligand, such as any PPAR gamma ligand described in U.S. patent application Publication No. 2001/0036955 A1.

Anti-Inflammatory Agents

Suitable anti-inflammatory agents include, but are not limited to, steroidal anti-inflammatory agents, and non-steroidal anti-inflammatory agents.

Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing.

Suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Anti-Fibrotic Agents

Suitable anti-fibrotic agents include, but are not limited to, an anti-angiogenic agent; a vascular endothelial growth factor (VEGF) antagonist; a basic fibroblast growth factor (bFGF) antagonist; a bFGF receptor antagonist; a transforming growth factor-beta (TGF-β) antagonist; a TGF-β receptor antagonist; a steroidal anti-inflammatory agent; and a non-pirfenidone TNF antagonist.

Combination Regimens

In one aspect, the present invention provides combination therapy for the treatment of a disorder amenable to treatment by inhibiting a SAPK in a cell in an individual. The following are non-limiting examples of possible combination regimens.

For example, a subject combination therapy comprises administering an effective amount of a Type II interferon receptor agonist, an effective amount of a pirfenidone or pirfenidone analog; detecting the level of SAPK activity in a biological sample from the individual; and adjusting the dose of the pirfenidone or pirfenidone analog based on the results of the detection step. In some embodiments, the method employs a Type II interferon receptor agonist that is IFN-gamma (IFN-γ).

In some embodiments, the invention provides a method using an effective amount of IFN-γ, and an effective amount of pirfenidone or a specific pirfenidone analog, in the treatment of a disorder in a patient comprising co-administering to the patient a dosage of IFN-γ containing an amount of about 10 µg to about 300 µg of drug per dose of IFN-γ, subcutaneously qd, qod, tiw, or biw, or per day substantially continuously or continuously; and a first dosage of pirfenidone or a pirfenidone analog in the range of about 5 mg/kg of body weight to about 125 mg/kg of body weight, or a first fixed dosage of pirfenidone or a specific pirfenidone analog in the range of about 400 mg to about 3600 mg in a single dose or two or three divided doses, administered orally qd for the desired treatment duration, for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 µg to about 300 µg of drug per dose of IFN-γ, subcutaneously qd, qod, tiw, or biw, or per day substantially continuously or continuously; and a first dosage of pirfenidone or a pirfenidone analog in the range of about 5 mg/kg of body weight to about 125 mg/kg of body weight in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 µg to about 300 µg of drug per dose of IFN-γ, subcutaneously qd, qod, tiw, or biw, or per day substantially continuously or continuously; and a first fixed dosage of pirfenidone or a pirfenidone analog in the range of from about 400 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 1200 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 800 mg to about 2400 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 400 mg to about 1200 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 100 μg of drug per dose of IFN-γ, subcutaneously qd, qod, tiw, or biw, or per day substantially continuously or continuously; a first fixed dosage of pirfenidone or a pirfenidone analog in the range of from about 400 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 100 μg of drug per dose of IFN-γ, subcutaneously qd, qod, tiw, or biw, or per day substantially continuously or continuously; a first fixed dosage of pirfenidone or a pirfenidone analog in the range of from about 1200 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 100 μg of drug per dose of IFN-γ, subcutaneously qd, qod, tiw, or biw, or per day substantially continuously or continuously; a first fixed dosage of pirfenidone or a pirfenidone analog in the range of from about 800 mg to about 2400 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 10 μg to about 100 μg of drug per dose of IFN-γ, subcutaneously qd, qod, tiw, or biw, or per day substantially continuously or continuously; a first fixed dosage of pirfenidone or a pirfenidone analog in the range of from about 400 mg to about 1200 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an pirfenidone or a specific pirfenidone analog, in the treatment of a disorder in a patient, comprising administering to the patient a dosage of IFN-γ containing an amount of about 200 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 400 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, an effective amount of pirfenidone or a specific pirfenidone analog, in the treatment of a disorder in a patient, comprising administering to the patient a dosage of IFN-γ containing an amount of about 200 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 1200 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 200 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 800 mg to about 2400 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a dosage of IFN-γ containing an amount of about 200 μg to about 300 μg of drug per dose of IFN-γ, subcutaneously qd, qod, tiw, or biw, or per day substantially continuously or continuously; a first fixed dosage of pirfenidone or a pirfenidone analog in the range of from about 400 mg to about 1200 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a total weekly dosage of IFN-gamma containing an amount of about 100 μg to about 1,500 μg of drug per week in divided doses administered subcutaneously qd, qod, tiw, biw, or administered substantially continuously or continuously; a first fixed dosage of pirfenidone or a pirfenidone analog in the range of from about 400 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a total weekly dosage of IFN-gamma containing an amount of about 100 µg to about 1,500 µg of drug per week in divided doses administered subcutaneously qd, qod, tiw, biw, or administered substantially continuously or continuously; a first fixed dosage of pirfenidone or a pirfenidone analog in the range of from about 1200 mg to about 3600 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a total weekly dosage of IFN-gamma containing an amount of about 100 µg to about 1,500 µg of drug per week in divided doses administered subcutaneously qd, qod, tiw, biw, or administered substantially continuously or continuously; a first fixed dosage of pirfenidone or a pirfenidone analog in the range of from about 800 mg to about 2400 mg in a single dose or two or three divided doses, administered orally qd for a first period of time; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In another embodiment, the invention provides a method using an effective amount of IFN-γ, and an effective amount of pirfenidone or a specific pirfenidone analog, in the treatment of a disorder in a patient, comprising administering to the patient a total weekly dosage of IFN-gamma containing an amount of about 100 µg to about 1,500 µg of drug per week in divided doses administered subcutaneously qd, qod, tiw, biw, or administered substantially continuously or continuously; a first fixed dosage of pirfenidone or a pirfenidone analog in the range of from about 400 mg to about 1200 mg in a single dose or two or three divided doses, administered orally qd for the desired treatment duration; detecting the level of SAPK activity in a biological sample from the individual; and adjusting the dose of the pirfenidone or pirfenidone analog based on the results of the detection step. In some embodiments, the method further comprises administering a second dosage of pirfenidone or pirfenidone analog for a second period of time, which second dosage is greater than the first dosage. In other embodiments, the method further comprises administering a second dosage of pirfenidone or pirfenidone analog for a second period of time, which second dosage is the same as the first dosage. In general, the IFN-γ treatment is continued along with the second dosage of pirfenidone treatment.

In any of the above-described regimens, a side effect management agent is administered, which side effect management agent can be selected from the group of a NSAID (e.g., aspirin, ibuprofen, acetaminophen); a histamine type 2 receptor antagonist; a hematopoietic agent; and an antacid. Suitable dosages for the use of such side effect management agents are well known in the art. For example, the dosages indicated on the label and/or package insert of any commercially available product having as its active ingredient any such side effect management agent can be used when practicing any of the above-described regimens.

Subjects Suitable for Treatment

Individuals who are suitable for treatment according to a subject method for treating a viral infection include individuals who have been clinically diagnosed with a viral infection; individuals who have been exposed to an individual having a viral infection; individuals who are at risk of contracting a viral infection; and the like.

Individuals who are suitable for treatment according to a subject method for treating a fibrotic disorder include individuals who have been clinically diagnosed with fibrosis, as well as individuals who have not yet developed clinical fibrosis but who are considered at risk of developing fibrosis.

Individuals who are suitable for treatment with a subject method for treating cancer include individuals having any type of cancer, including individuals who have been diagnosed with a cancer and who have not yet been treated for the cancer; individuals who have been diagnosed with a cancer, and who have been treated for the cancer with a treatment regimen other than a subject treatment regimen, including individuals who have failed previous treatment regimens for the cancer; and individuals who have been diagnosed with a cancer, and who have been treated with the cancer such that the cancer is in remission, but who are at risk for re-growth of the cancer.

Individuals who are suitable for treatment with a subject method for treating an angiogenic disorder include individuals having any type of angiogenic disorder, including individuals who have been diagnosed with an angiogenic disorder and who have not yet been treated for the angiogenic disorder; individuals who have been diagnosed with an angiogenic disorder, and who have been treated for the angiogenic disorder with a treatment regimen other than a subject treatment regimen, including individuals who have failed previous treatment regimens for the angiogenic disorder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Pirfenidone Inhibits SAPK Enzymatic Activity

Enzymatic activity of various human kinases was assayed in the presence and the absence of pirfenidone. Percent enzyme activity of various human enzymes in the presence of substrate and pirfenidone are shown in FIGS. 1-5, and in Table 2, below, where "percent enzyme activity" is the percent of the control activity (e.g., in the absence of pirfenidone):

TABLE 2

| Target enzyme | % Activity |
| --- | --- |
| SAPK3 | 46 |
| CSK | 64 |
| SAPK2α | 70 |
| SAPK2β | 74 |
| Syk | 78 |
| MKK6 | 84 |
| CHK2 | 84 |
| Bmx | 86 |
| CDK3/cyclinE | 86 |
| Rsk1 | 88 |
| PKBα | 88 |
| PKBβ | 88 |
| PKCη | 88 |
| Fes | 88 |
| CDK2/cyclinE | 89 |
| PRK2 | 90 |
| ROCK-II | 90 |
| IKKβ | 90 |
| PRAK | 90 |
| GSK3α | 91 |
| GSK3β | 91 |
| c-RAF | 91 |
| cSRC | 91 |
| Lyn | 92 |
| CDK2/cyclinA | 92 |
| CDK7/cyclinD3 | 92 |
| IGF-1R | 92 |
| PAK2 | 93 |
| MSK1 | 93 |
| Axl | 93 |
| PDK1 | 93 |
| PKCα | 94 |
| CK2 | 94 |
| CDK7/cyclinH/MAT1 | 95 |
| PKCa | 96 |
| PKCτ | 96 |
| p70S6K | 96 |
| PKCµ | 96 |
| JNK2 | 97 |
| IR | 97 |
| Fyn | 97 |
| MAPKAP-K2 | 97 |
| SAPK4 | 98 |
| MAPK1 | 98 |
| PKD2 | 98 |
| Rsk2 | 99 |
| PKCβII | 100 |
| MAPK2 | 100 |

TABLE 2-continued

| Target enzyme | % Activity |
| --- | --- |
| MEK1 | 100 |
| PDGFR | 101 |
| TrkB | 101 |
| PDGFRβ | 101 |
| CDK1/cyclinB | 102 |
| CDK5/cyclinB | 102 |
| PKCδ | 102 |
| Flt3 | 103 |
| FGFR3 | 104 |
| Yes | 104 |
| Lck | 104 |
| CHK1 | 105 |
| MKK7β | 105 |
| JNK1 | 105 |
| JNK3 | 106 |
| SGK | 106 |
| PKCo | 106 |
| CaMKIV | 107 |
| ZAP-70 | 109 |
| PKA | 109 |
| PKBγ | 111 |
| IKKα | 114 |
| Rsk3 | 115 |
| Aurora-A | 120 |

The data indicate that pirfenidone is an inhibitor of SAPK, but does not substantially inhibit other kinases tested.

Example 2

Pirfenidone does not Affect IFN-γ-Induced STAT1 Tyrosine Phosphorylation

Materials and Methods

Cytokines, Antibodies, and Reagent

Tissue culture plates were purchased from Falcon (Lincoln Park, N.J.). DMEM (Dulbecco's Modified Eagle's Medium) and other cell culture reagents, polyacrylamide gel electrophoresis (PAGE) reagents were purchased from Sigma (St. Louis, Mo.). IFN-γ (Actimune) and Pirfenidone (PFD) were from InterMune Inc. The anti-human phospho-STAT1 and STAT1 antibodies and horse-radish peroxidase-coupled secondary Abs were purchased from Cell Signaling (Beverly, Mass.). Nitrocellulose sheets (Hybond-C Ext), ECL (enhanced chemiluminescent) reagents and X-Ray films were purchased from Amersham (Aylesbury, United Kingdom).

Testing the Effect of Pirfenidone on STAT1 Tyrosine Phosphorylation

Figure 6:
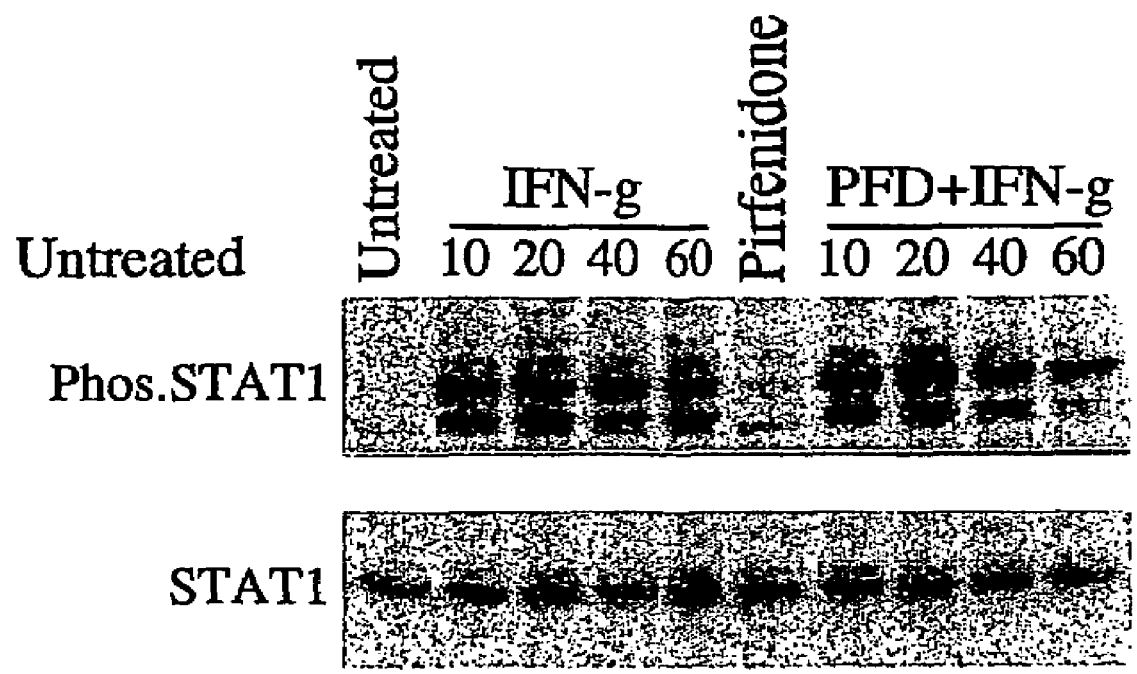
FIG. 6 depicts results showing that pirfenidone does not affect IFN-γ-induced STAT1 tyrosine phosphorylation.

ME180 cells were grown in DMEM supplemented with 10% heat inactivated fetal calf serum, 2 mM L-glutamine, streptomycin (100 µg/ml) and penicillin (100 units/ml). Briefly, cells were seeded at a density of $5 \times 10^6$ cells in 100 mm tissue culture dishes. After 24 hrs, cells were washed with phosphate-buffered saline (PBS) and incubated in serum free growth media for 16 hours, then treated with medium or with 100 µg/ml of Pirfenidone for 1 h before treating them with Actimune (10 ng/ml) for 0-10-20-40 and 60 min. At the end of incubation period, cells were lysed by incubation in 50 mM HEPES (pH 7.0) containing 100 mM NaCl, 1.2% Triton X-100, 10% glycerol, 1.5 mM $MgCl_2$, 100 mM NaF, 10 mM sodium pyrophosphate, 1 mM sodium orthovanadate, 1 mM EGTA (ethylene glycol-bis-β-aminoethylether-tetraacetic acid), 1 mM DTT (dithiothreitol), 1 mM phenylmethylsulfonylfluoride (PMSF), 0.15 unit/ml aprotinin, 10 µg/ml leupeptin, 10 µg/ml pepstatin. Lysates were clarified by centrifugation (12.000×g for 1 min.). Equal amounts (100 µg) total proteins were subjected to SDS-PAGE on 10% polyacrylamide gels to separate the proteins. The proteins were then electrophoretically transferred from the polyacrylamide gel onto a nitrocellulose sheet for overnight at 20 mAmp, and analyzed by immunoblotting with anti-phospho STAT1-specific antibody (antibody specific for phosphorylated STAT1). The blot was then stripped off and re-labeled with STAT1 antibody for even loading. The results are shown in FIG. 6. FIG. 6: Pirfenidone does not affect IFN-γ-induced STAT1 tyrosine phosphorylation.

Serum-starved ME180 cells were treated with medium or with 100 μg/ml of pirfenidone for 1 h., then 10 ng/ml IFN-γ was added. Cellular lysates were collected at different time points. 100 μg of total lysate was fractionated on 10% SDS-PAGE, proteins were immunoblotted overnight at 20 mAmp. The blot was labeled with antibody specific for phosphorylated form of STAT 1, then the blot was stripped off and re-labeled with STAT1 antibody for even loading.

Example 3

Assaying SAPK Activity in Peripheral Blood Mononuclear Cells

Materials and Methods

Cytokines, Antibodies, and Reagent

Tissue culture flasks are purchased from Falcon (Lincoln Park, N.J.). RPMI-1640 growth medium and other cell culture reagents, PAGE polyacrylamide gel electrophoresis reagents, TNF-α is purchased from Sigma (St. Louis, Mo.). The anti-human monoclonal antibody for CREB, and protein A/G-agarose are purchased from Santa Cruz Biotechnology (Santa Cruz, Calif.). γ-$^{32}$P-ATP, Nitrocellulose sheets (Hybond-C Ext) and ECL reagents are purchased from Amersham (Aylesbury, United Kingdom).

Cell Culture and Treatments:

Peripheral Blood Mononuclear Cells (PBMC) are collected from patients treated with Pirfenidone (600 mg/3 times/d) or with placebo. PBMC are incubated in RPMI-1640 supplemented with 10% heat inactivated fetal calf serum, 2 mM L-glutamine, streptomycin (100 μg/ml) and penicillin (100 units/ml) for 3 hours. Then, $2\times10^7$ cells are treated with 1 μM γ-$^{32}$P-ATP and TNF-α (10 ng/ml) for 0 minutes, 5 minutes, 15 minutes, 30 minutes, or 45 minutes. At the end of the incubation period, cells are lysed by incubation in 50 mM HEPES (pH 7.0) containing 100 mM NaCl, 1.2% Triton X-100, 10% glycerol, 1.5 mM $MgCl_2$, 100 mM NaF, 10 mM sodium pyrophosphate, 1 mM sodium orthovanadate, 1 mM EGTA (ethylene glycol-bis-β-aminoethylether-tetraacetic acid), 1 mM DTT, 1 mM phenylmethylsulfonylfloride, 0.15 unit/ml aprotinin, 10 μg/ml leupeptin, and 10 μg/ml pepstatin. Lysates are clarified by centrifugation (12.000×g for 1 min.). Next, 3 mg of lysate are pre-cleared with 100 μl of protein A/G agarose beads for 1 h. at 4° C. Next, samples are centrifuged, 3 μg of anti-CREB antibodies are added to supernatants, and samples are shaken at 4° C. for 4 h. Next, 100 μl of protein A/G agarose beads are added and samples are shaken overnight at 4° C. Beads are precipitated by centrifugation, and washed three times with cell lysis buffer. Next, 100 μl of 2×SDS-loading dye are added onto the pellets, then samples are boiled for 5 min, and centrifuged. Equal amount of supernatants are subjected to SDS-PAGE on 10% polyacrylamide gels to separate proteins. Following electrophoresis, the proteins are electrophoretically transferred from the acrylamide gel onto nitrocellulose sheet for overnight at 20 mAmp. X-Ray film is exposed to the blot and developed. Parallel to this, an identical gel is prepared from regular cellular lysate and the blot is labeled with anti CREB antibody to determine the exact position of CREB on the gel.

Results

Transcription factor CREB is robustly activated by several stress inducing environmental stimuli, including TNF-α, UV-C, and osmotic shock. It is expected that there is very little phosphorylation of CREB before treatment of PBMC with TNF-α. It is expected that when PBMC are treated with TNF-α, the phosphorylation of CREB increases in a time-dependent manner with the highest level (~5 fold vs control) of phosphorylation at 15 min. It is also expected that TNF-α-induced phosphorylation of CREB in PBMC isolated from Pirfenidone treated patients is only ~1.5-2.0 fold higher than that of untreated cells.

The effect of Pirfenidone on the activity of SAPK2/3 is analyzed. It is expected that 100 μg/ml of Pirfenidone inhibits the activity of SAPK2/3 by 50% under in vitro condition. It is expected that the in vivo target of Pirfenidone is SAPK2/3.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disorder in an individual, the method comprising administering to an individual who has the disorder an effective amount of pirfenidone or a pirfenidone analog; comparing a post-treatment level of stress-activated protein kinase (SAPK) activity in a biological sample from the individual to a pre-treatment level of SAPK activity; and adjusting the dose of the pirfenidone or pirfenidone analog based on the results of the comparison step; wherein the disorder is selected from the group consisting of fibrotic disorder, carcinoma, sarcoma, leukemia, lymphoma, viral infection, inflammatory disorder and TNF-mediated disorder, and wherein said carcinoma is selected from the group consisting of esophageal carcinoma, hepatocellular carcinoma, basal cell carcinoma, bladder carcinoma, including transitional cell carcinoma which is a malignant neoplasm of the bladder, squamous cell carcinoma, bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

2. The method of claim 1, wherein the post-treatment SAPK activity level is from about 10% to about 40% lower than the pre-treatment SAPK activity level, and wherein the adjusting step comprises administering a second dosage of pirfenidone or pirfenidone analog that is at least about 10% higher than the first dosage of pirfenidone or pirfenidone analog.

3. The method of claim 1, wherein the biological sample is peripheral blood mononuclear cells.

4. The method of claim 1, wherein said fibrotic disorder is pulmonary fibrosis, renal fibrosis, liver fibrosis, or heart fibrosis.

5. The method of claim 1, further comprising administering an effective amount of a Type II interferon receptor agonist.

6. The method of claim 5, wherein the Type II interferon receptor agonist is IFN-γ.

7. The method of claim 1, further comprising administering an effective amount of a Type I interferon receptor agonist.

8. The method of claim 7, wherein the Type I interferon receptor agonist is IFN-α.

9. A method of treating a disorder in an individual, the method comprising administering to an individual who has the disorder an effective amount of pirfenidone or a pirfenidone analog; comparing a second post-treatment level of stress-activated protein kinase (SAPK) activity in a biological sample from the individual to a first post-treatment level of SAPK activity; and adjusting the dose of the pirfenidone or pirfenidone analog based on the results of the comparison step; wherein the disorder is selected from the group consisting of fibrotic disorder, carcinoma, sarcoma, leukemia, lymphoma, viral infection, inflammatory disorder and TNF-mediated disorder, and wherein said carcinoma is selected from the group consisting of esophageal carcinoma, hepatocellular carcinoma, basal cell carcinoma, bladder carcinoma, including transitional cell carcinoma which is a malignant neoplasm of the bladder, squamous cell carcinoma, bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

10. A method of inhibiting a stress-activated protein kinase enzymatic activity in a cell of an individual, the method comprising administering to an individual in need thereof an effective amount of pirfenidone or a pirfenidone analog; comparing a post-treatment level of stress-activated protein kinase (SAPK) activity in a biological sample from the individual to a pre-treatment level of SAPK activity; and adjusting the dose of the pirfenidone or pirfenidone analog based on the results of the comparison step: wherein the individual in need thereof has a disorder selected from the group consisting of fibrotic disorder, carcinoma, sarcoma, leukemia, lymphoma, viral infection, inflammatory disorder and TNF-mediated disorder, and wherein said carcinoma is selected from the group consisting of esophageal carcinoma, hepatocellular carcinoma, basal cell carcinoma, bladder carcinoma, including transitional cell carcinoma which is a malignant neoplasm of the bladder, squamous cell carcinoma, bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

11. The method of claim 1, wherein the carcinoma comprises a solid tumor.

12. The method of claim 1, wherein the sarcoma comprises a solid tumor.

13. The method of claim 1, wherein the leukemia comprises a solid tumor.

14. The method of claim 1, wherein the lymphoma comprises a solid tumor.

15. The method of claim 11, wherein the pirfenidone or pirfenidone analog are administered as adjuvant therapy to a primary carcinoma therapy.

16. The method of claim 12, wherein the pirfenidone or pirfenidone analog are administered as adjuvant therapy to a primary sarcoma therapy.

17. The method of claim 13, wherein the pirfenidone or pirfenidone analog are administered as adjuvant therapy to a primary leukemia therapy.

18. The method of claim 14, wherein the pirfenidone or pirfenidone analog are administered as adjuvant therapy to a primary lymphoma therapy.

* * * * *